United States Patent [19]

Lepone

[11] 4,454,135

[45] Jun. 12, 1984

[54] ORGANOTIN INSECTICIDAL SULFONAMIDES

[75] Inventor: Gerald E. Lepone, Wilmington, Del.

[73] Assignee: E. I. Du Pont de Nemours and Company, Wilmington, Del.

[21] Appl. No.: 455,505

[22] Filed: Jan. 4, 1983

[51] Int. Cl.³ .................. A01N 55/04; C07F 7/22
[52] U.S. Cl. .................. 424/245; 260/429.7; 544/64; 544/225
[58] Field of Search ............ 544/64, 225; 260/429.7; 424/245

[56] References Cited

U.S. PATENT DOCUMENTS 4,212,810 7/1980 Gitlitz et al. .............. 260/429.7 X Primary Examiner—Richard Raymond

[57] ABSTRACT

Novel tetraorganotin benzenesulfonamide compounds are described which possess insecticidal and arachnicidal activity. In addition, novel trifluoroacetate organotin benzenesulfonamide intermediates useful in the synthesis of these tetraorganotin benzenesulfonamide compounds are described.

20 Claims, No Drawings

4,454,135

ORGANOTIN INSECTICIDAL SULFONAMIDES

TECHNICAL FIELD

This invention relates to certain novel organotin benzenesulfonamide compounds, to compositions containing such compounds, and to a method of use of such compositions to control insect and arachnid pests.

BACKGROUND OF THE INVENTION

Pests such as insects and arachnids are a constant irritation and threat to man. They injure and destroy plants, consume stored food supplies, damage useful organic materials such as wood and wool, directly set upon man and animals and invade their dwellings contributing to the spread of some of the most serious and harmful diseases. A major factor in the control of such pest organisms is the agrichemical. There is a continuing need for new agrichemicals to replace those to which pest organisms have become resistant. There is always a need for chemicals possessing greater activity or which are active against a broader variety of pests.

Organotin compounds have been found to be effective against a variety of arthropod pests [Blum, M. S., *J. Econ. Entymol.*, Vol. 53, 445 (1960)]. Trialkyltin compounds, i.e. those with three (3) hydrocarbon radicals bonded to a tin atom, are known to be useful against certain species of arthropods. U.S. Pat. No. 3,264,177 discloses tricyclohexyltin compounds which effectively control arachnids, but not insects. Other trialkyltin compounds, e.g., those disclosed in U.S. Pat. No. 3,702,360 which are effective insecticides, possess high phytotoxicity.

Tetraorganotin compounds, those containing four (4) hydrocarbon groups bonded to the tin atom, have unexpectedly been found to possess biological activity. U.S. Pat. Nos. 4,138,483; 4,212,810; 4,212,885; 4,316,853 and foreign equivalents thereof commonly assigned to M&T Chemicals, Inc. disclose trimethyl substituted, tetraorganotin compounds in which the fourth carbon-tin bond is to a substituted phenyl, benzyl, or heterocyclic moiety. Included within the M&T patents are compounds of the formulae:

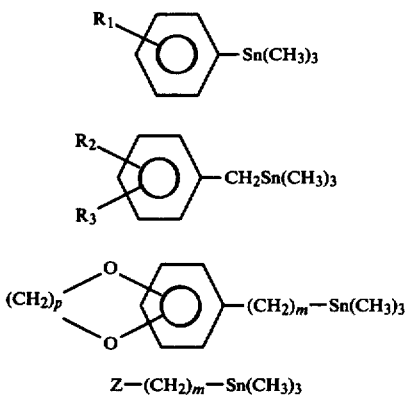

where $R_1$ is $CO_2^-Y^+$, $CO_2R_4$, $SO_2OR_5$, $SO_2R_5$, $SO_3^-Y^+$, $PO(OR_5)OR_6$, or $PO(R_5)R_6$;

$R_2$ and $R_3$ are H, F, Cl, Br, I, aryl, $OR_4$, $SR_5$, $NR_6R_7$, $NR_5R_6R_7^+X^-$, acetyl, $CO_2H$, $CO_2^-Y^+$, $CO_2R_4$, $SO_2OR_5$, $SO_2R_5$, $SO_3^-Y^+$, $PO(OR_5)OR_6$, $PO(R_5)R_6$, or CN, with the proviso that both $R_2$ and $R_3$ cannot be H;

$R_4$ is $C_1$-$C_{12}$ alkyl;

$R_5$, $R_6$, and $R_7$ are H or $C_1$-$C_{12}$ alkyl;

$X^-$ is bromide, iodide, bisulfate, acetate, or methyl sulfate;

$Y^+$ is alkali metal or ammonium;

Z is

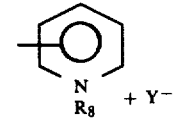

or an aromatic mono- or bicyclic heterocyclic group wherein each ring contains 5 or 6 atoms including one or two hetero atoms selected from N, O, and S, provided that Z cannot be pyridyl, furyl, or thienyl when m is 0 and the heterocyclic groups must be free of active hydrogen;

m is 0 or 1; and p is 1 or 2.

Japanese Patent 57-072,905, assigned to Sumitomo, discloses insecticidal and herbicidal compounds of the formula:

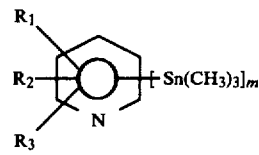

where $R_1$, $R_2$, and $R_3$ are H or lower alkyl, or $R_2$ and $R_3$ taken together may form a quinoline ring; and m is 1 or 2.

SUMMARY OF THE INVENTION

According to this invention, there are provided novel tetraorganotin sulfonamide compounds and their agriculturally suitable salts which possess broad arthropocidal activity. The compounds of the instant invention are not limited to trimethyl substitution, and they represent novel structures in that all incorporate the sulfonamide moiety, a substituent not included in the teaching of the M&T patents. The compounds of the instant invention possess a broad spectrum of activity in controlling both insects and arachnids. A broad spectrum of activity with minimal plant phytotoxicity and mammalian toxicity are currently desirable features for arthropocidal compounds. Specifically, one aspect of this invention relates to compounds having the Formula:

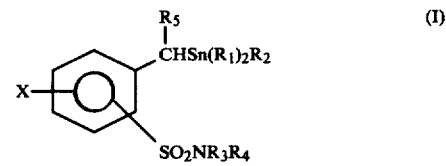

wherein $R_1$ and $R_2$ are independently $C_1$-$C_3$ alkyl;

$R_3$ is H, $OCH_3$, $C_1$-$C_{20}$ alkyl, $C_5$-$C_6$ cycloalkyl optionally substituted with $CH_3$ or $OCH_3$, $C_1$-$C_3$ alkyl optionally substituted with $OCH_3$ or $OC_2H_5$, or

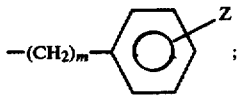

$R_4$ is H, $C_1$-$C_{20}$ alkyl, $C_5$-$C_6$ cycloalkyl optionally substituted with $CH_3$ or $OCH_3$, $C_1$-$C_3$ alkyl optionally substituted with $OCH_3$ or $OC_2H_5$, or

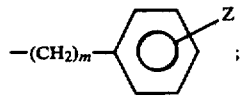

or $R_3$ and $R_4$ may be taken together to form

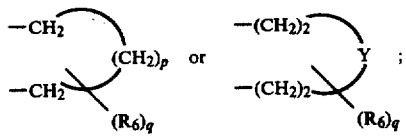

$R_5$ is H or $CH_3$;
$R_6$ is $CH_3$;
X is H, F, Cl, $CH_3$ or $OCH_3$;
Y is O or $NR_7$;
Z is H, F, Cl, $CH_3$ or $OCH_3$;
$R_7$ is $C_1$-$C_3$ alkyl;
m is 0 or 1;
p is 2, 3 or 4; and
q is 0, 1 or 2;
or an agriculturally suitable salt thereof; provided that:
(1) the total number of carbons in $R_3$ and $R_4$ is no greater than 20;
(2) when either $R_3$ or $R_4$ is

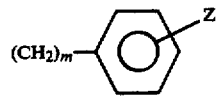

and the other is alkyl, the total number of carbons in $R_3$ and $R_4$ is no greater than 12; and
(3) when $R_3$ is $OCH_3$, then $R_4$ is H or $C_1$-$C_4$ alkyl.

Another aspect of this invention relates to novel intermediates having the Formula:

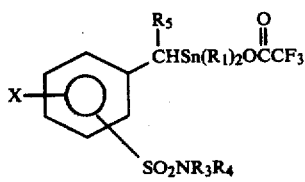

wherein
$R_1$ is $C_1$-$C_3$ alkyl;
$R_3$ is H, $OCH_3$, $C_1$-$C_{20}$ alkyl, $C_5$-$C_6$ cycloalkyl optionally substituted with $CH_3$ or $OCH_3$, $C_1$-$C_3$ alkyl optionally substituted with $OCH_3$ or $OC_2H_5$, or

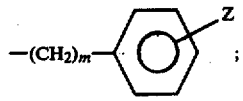

$R_4$ is H, $C_1$-$C_{20}$ alkyl, $C_5$-$C_6$ cycloalkyl optionally substituted with $CH_3$ or $OCH_3$, $C_1$-$C_3$ alkyl optionally substituted with $OCH_3$ or $OC_2H_5$, or

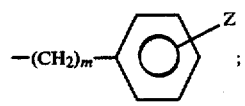

or $R_3$ and $R_4$ may be taken together to form

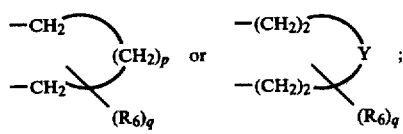

$R_5$ is H or $CH_3$;
$R_6$ is $CH_3$;
X is H, F, Cl, $CH_3$ or $OCH_3$;
Y is O or $NR_7$;
Z is H, F, Cl, $CH_3$ or $OCH_3$;
$R_7$ is $C_1$-$C_3$ alkyl;
m is 0 or 1;
p is 2, 3 or 4; and
q is 0, 1 or 2;
provided that:
(1) the total number of carbons in $R_3$ and $R_4$ is less than or equal to 20;
(2) when either $R_3$ or $R_4$ is

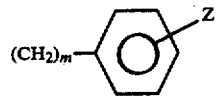

and the other is alkyl, the total number of carbons in $R_3$ and $R_4$ is less than or equal to 12; and
(3) when $R_3$ is $OCH_3$, then $R_4$ is H or $C_1$-$C_4$ alkyl.

These intermediates are for use in synthesizing tetraorganotin arthropodicidal compounds wherein $R_1 \neq R_2$. Specifically preferred in order of increasing preference for their high insecticidal or arachnicidal activity, or ease of synthesis, or both, are:
(1) the compounds of Formula I wherein
$R_1 = R_2$; and
$R_5$ is H;
(2) compounds of preference (1) wherein X is H;
(3) compounds of preference (2) wherein
$R_1$ and $R_2$ are $CH_3$;
$R_3$ is H, $C_1$-$C_{20}$ alkyl, $C_5$-$C_6$ cycloalkyl optionally substituted with $CH_3$ or $OCH_3$, $CH_2CH_2OCH_3$, $CH_2CH_2OC_2H_5$, $CH_2CH_2CH_2OCH_3$, $CH_2CH_2CH_2OC_2H_5$, or

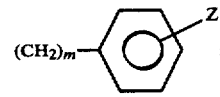

and $R_4$ is H, $C_1$–$C_{20}$ alkyl, $C_5$–$C_6$ cycloalkyl optionally substituted with $CH_3$ or $OCH_3$, $CH_2CH_2OCH_3$, $CH_2CH_2OC_2H_5$, $CH_2CH_2CH_2OCH_3$, or $CH_2CH_2CH_2OC_2H_5$;

or $R_3$ and $R_4$ may be taken together to form

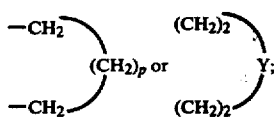

Y is O or $NCH_3$; and
p is 2 or 3.

Specifically preferred are:
(1) 2-[(trimethylstannyl)methyl]benzenesulfonamide;
(2) N-methyl-2-[(trimethylstannyl)methyl]benzenesulfonamide;
(3) N,N-dimethyl-2-[(trimethylstannyl)methyl]benzenesulfonamide;
(4) N-butyl-2-[(trimethylstannyl)methyl]benzenesulfonamide;
(5) N-(1,1-dimethylethyl)-2-[(trimethylstannyl)methyl]benzenesulfonamide;
(6) N-ethyl-N-methyl-2-[(trimethylstannyl)methyl]benzenesulfonamide;
(7) N,N-dihexyl-2-[(trimethylstannyl)methyl]benzenesulfonamide;
(8) N-dodecyl-2-[(trimethylstannyl)methyl]benzenesulfonamide;
(9) N-phenyl-2-[(trimethylstannyl)methyl]benzenesulfonamide;
(10) 4-[2-[(trimethylstannyl)methyl]phenylsulfonyl]morpholine;
(11) 1-[2-[(trimethylstannyl)methyl]phenylsulfonyl]pyrrolidine;
(12) N-methyl-4-[(trimethylstannyl)methyl]benzenesulfonamide; and
(13) N,N-dimethyl-4-[(trimethylstannyl)methyl]benzenesulfonamide.

Another aspect of this invention relates to a composition suitable for the control of insects and arachnids which comprises an insecticidally or arachnicidally effective amount of the compounds of Formula I and a diluent, surfactant, or mixtures thereof. Yet another aspect of the invention relates to a method for the control of insects and arachnids which comprises applying to insects or arachnids, to a habitat thereof, or to a locus to be protected an insecticidally or arachnicidally effective amount of a compound of Formula I.

DETAILED DESCRIPTION SYNTHESIS

The compounds of Formula I are readily prepared from the appropriate sulfonamides of Formula IIa as outlined in Equation 1, where $R_1$, $R_2$, $R_3$, $R_4$, $R_5$ and X are as previously defined.

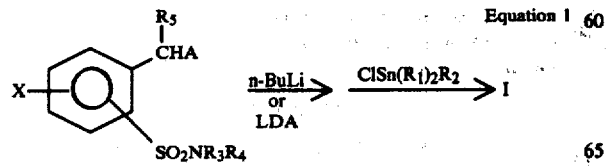

A = H, Br

For the compounds of Formula IIa where A=H, treatment with an alkyllithium reagent, for example n-butyllithium, or lithium diisopropylamide (LDA) will give α-deprotonation. Trapping with the appropriate trialkylstannyl chloride will yield the corresponding trialkylstannylmethylbenzenesulfonamides of Formula I. (For a general review of ortho-lithiation see: Organic Reactions, Vol. 26, John Wiley and Sons, Inc., New York, 1979, pp. 1–360.) When A=Br, reaction with an alkyllithium reagent will result in lithium-halogen exchange, as is well known in the literature.

Alternatively, compounds of Formula I may be synthesized from the sulfonamides IIb as shown in Equation 2. The compounds of Formula III can be readily prepared from the corresponding distannanes and lithium or sodium metal.

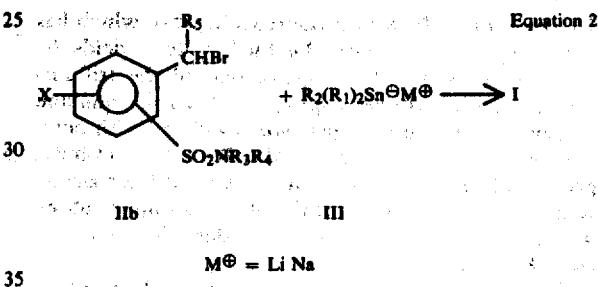

$M^\oplus$ = Li Na

The compounds of Formula I may also be prepared from sulfonamides IIc and the appropriate chloromethyltrialkylstannanes IV as outlined in Equation 3. The compounds of Formula IV may be prepared by methods known in the art [for example, see D. Seyferth et al., J. Organometallic Chem., 30, 151 (1971)].

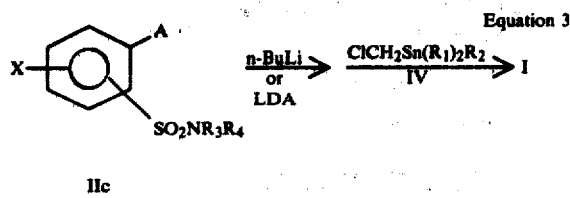

A = H, Br

The compounds of Formula Ia where $R_1=R_2$ may also serve as intermediates to the compounds of Formula Ib where $R_1 \neq R_2$ as shown in Equation 4.

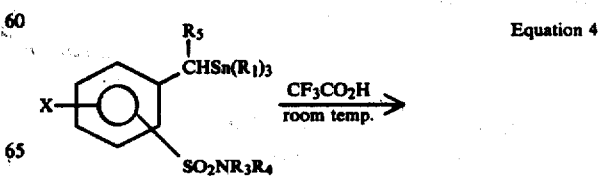

-continued

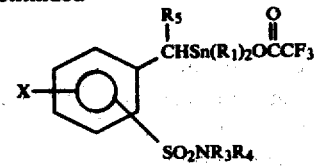

V

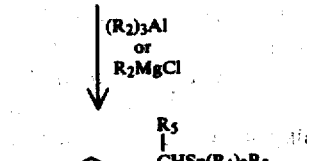

Ib $R_1 \neq R_2$

The reaction of Ia with trifluoroacetic acid, which has not been previously reported in the literature, yields the novel intermediates V. Displacement of the trifluoroacetate group with an appropriate trialkyl aluminum reagent or Grignard reagent will yield Ib. With compounds of Formula Ia where either $R_3$ or $R_4$ is a t-butyl group and the other is H, reaction with trifluoroacetic acid will also lead to loss of the t-butyl group, resulting in the unsubstituted sulfonamides V and Ib ($R_3=R_4=H$).

The sulfonamides of Formula IIa are easily prepared from the corresponding sulfonyl chlorides of Formula VI as is well known in the art. The subsequent bromination of IIa to yield IIb may be accomplished by standard literature procedures and is outlined in Equation 5.

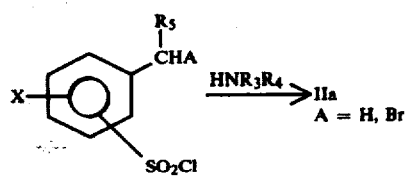

VI A = H, Br $$\xrightarrow{\text{Br}_2 \text{ or N—bromosuccinimide}}_{A=H} \text{IIb}$$

The preparation of benzenesulfonyl chlorides has been widely reported in the literature. For example, chlorination of the thiols of Formula VII or diazotization of the anilines of Formula VIII and subsequent coupling with sulfur dioxide is well known and is outlined in Equations 6 and 7.

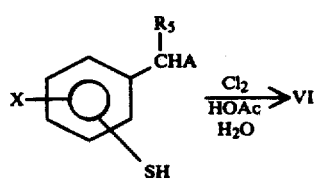

VII A = H, Br

-continued

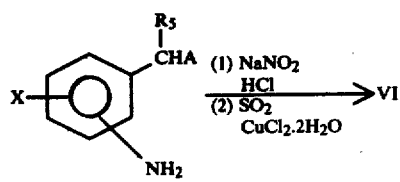

VIII A = H, Br

Lithiation of compounds of Formula IX and trapping with sulfuryl chloride will also yield the sulfonyl chlorides VIa as shown in Equation 8.

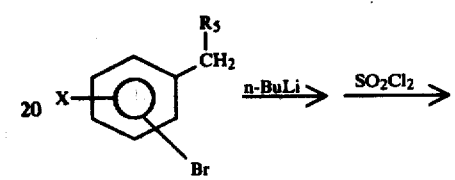

IX

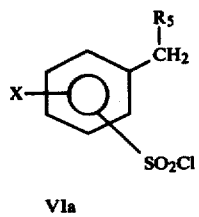

VIa

The compounds of Formula I wherein $R_3$ and $R_4$ are taken together to form

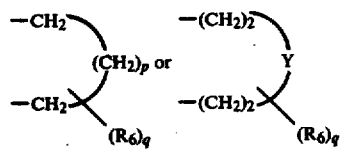

are synthesized by reacting the appropriate cyclic unsaturated amine with a sulfonyl chloride of Formula VI as shown in Equation 5.

Agriculturally suitable salts of compounds of Formula I are also useful insecticides and can be prepared by a number of ways known to the art. For example, metal salts can be made by treating compounds of Formula I wherein at least one of $R_3$ or $R_4$ is hydrogen with a solution of an alkali or alkaline earth salt having a sufficiently basic anion (e.g. hydroxide, alkoxide, carbonate or hydride).

The compounds of this invention and their preparation are further illustrated by the following examples wherein temperatures are given in degrees centigrade, and nuclear magnetic resonance (NMR) absorptions are reported as parts per million downfield from internal tetramethylsilane.

EXAMPLE 1

2-Methylbenzenesulfonyl chloride

To a solution of o-toluenethiol (114.8 g, 0.930 mol) in water (1100 ml) and acetic acid (455 ml) at −5° to 0° was added liquid chlorine (155 mol, 3.32 mol) at a rate to maintain an internal temperature less than 10°. When the addition was complete, the reaction mixture was stirred at 0° for ½ hour and at room temperature for 1 hour. The crude product was extracted into methylene chloride (4×200 ml), washed with saturated NaHCO₃ (300 ml) and 10% NaOH (2×100 ml), dried (MgSO₄), filtered and concentrated. Distillation gave 2-methylbenzenesulfonyl chloride as a light yellow oil, bp. 68°-70° (0.2-0.5 mm).

NMR (CDCl₃)δ: 2.8 (s, ArCH₃); and 7.2-8.2 (m, ArH).

EXAMPLE 2

N,2-Dimethylbenzenesulfonamide

To a solution of 2-methylbenzenesulfonyl chloride (37.4 g, 0.196 mol) in methylene chloride (300 ml) at −5° to 0° under nitrogen was added liquid methylamine (27.5 ml, 0.588 mol) at a rate to maintain an internal temperature less than 10°. The reaction mixture was stirred at 0° for ½ hour and then allowed to warm to room temperature. After 1¼ hours, filtration and concentration of the filtrate gave an oil which solidified upon cooling. Washing the solid with n-butyl chloride gave N,2-dimethylbenzenesulfonamide as a light yellow powder (28.4 g, 78%), mp. 62°-64°.

NMR (CDCl₃)δ: 2.65 (2s, Ar—CH₃ and N—CH₃); 5.9 (broad, NH); and 7.1-8.1 (m, Ar—H).

EXAMPLE 3

N-Methyl-2-[(trimethylstannyl)methyl]benzenesulfonamide

A solution of N,2-dimethylbenzenesulfonamide (3.70 g, 20.0 mmol) in dry tetrahydrofuran (75 ml) was cooled to −78° with stirring under nitrogen. n-Butyllithium in hexanes (1.6 M, 28 ml, 44 mmol) was added dropwise over ½ hour. After 2 hours at −78°, a solution of trimethyltin chloride (4.42 g, 22.0 mmol) in dry tetrahydrofuran (20 ml) was added dropwise. The reaction mixture was allowed to warm to 0° over 1 hour, and then 5% HCl (50 ml) was added dropwise at a rate to maintain an internal temperature less than 10°. After concentrating the reaction mixture in vacuo, the product was extracted into methylene chloride (3×100 ml), washed with water (2×200 ml), dried (MgSO₄), filtered and concentrated. Purification by flash chromatography (SiO₂, hexane/ethyl acetate, 8:2) gave N-methyl-2-[(trimethylstannyl)methyl]benzenesulfonamide (3.4 g, 49%) as a white powder, m.p. 59°-60°.

NMR (CDCl₃)δ: 0.0 (s, Sn(CH₃)₃); 2.6-2.7 (s and d, ArCH₂ and NCH₃); 4.8 (broad, NH); and 6.9-8.0 (m, ArH).

IR(KBr): 3340 (NH), 1470, 1310 (SO₂), 1160 (SO₂), 1080 and 760 cm⁻¹.

EXAMPLE 4

N,N-Dimethyl-4-[(trimethylstannyl)methyl]benzenesulfonamide

To a stirred solution of diisopropylamine (3.10 ml, 22.0 mmol) in dry tetrahydrofuran (25 ml) at −5° to 0° under nitrogen was added n-butyllithium in hexanes (1.6 M, 14 ml, 22 mmol). After ½ hour at 0°, the reaction mixture was cooled to −78° and treated with N,N-4-trimethylbenzenesulfonamide (3.98 g, 20.0 mmol) in dry tetrahydrofuran (25 ml). After 2½ hours at −78°, a solution of trimethyltin chloride (4.03 g, 20.0 mmol) in dry tetrahydrofuran (25 ml) was added dropwise. The reaction mixture was allowed to warm to 0° over 1 hour, acidified with 5% HCl, and then concentrated in vacuo. The crude product was extracted into methylene chloride (400 ml), washed with water (3×250 ml), dried (MgSO₄), filtered and concentrated. Washing the solid with hexanes gave N,N-dimethyl-4-[(trimethylstannyl)methyl)]benzenesulfonamide (3.56 g) as a white powder, m.p. 63°-66°.

NMR (CDCl₃)δ: 0.1 (s, Sn(CH₃)₃); 2.4 (s, ArCH₂); 2.7 (s, N(CH₃)₂); and 7.1 and 7.6 (ABq, Ar—H).

IR (KBr): 1590, 1340 (SO₂), 1160 (SO₂), 1070, 950 and 840 cm⁻¹.

EXAMPLE 5

2-[(Dimethyl)hydroxystannyl(methyl)]benzenesulfonamide, ester with 2,2,2-trifluoroacetic acid A solution of N-(1,1-dimethylethyl)-2-[(trimethylstannyl)methyl)]benzenesulfonamide (3.2 g, 8.2 mmol, prepared by methods taught in Examples 1-3) in trifluoacetic acid was stirred at room temperature under nitrogen. After 15 hours, the solvent was removed in vacuo, carbon tetrachloride was added, and the solvent was again removed in vacuo. Trituration with hexane and washing with n-butyl chloride gave the product as a white powder, m.p. 118°-121°.

NMR (CDCl₃)δ: 0.5 (s, Sn(CH₃)₂); 2.95 (s, ArCH₂); 5.2 (broad, NH₂); and 7.1-8.1 (m, Ar—H).

IR (KBr): 3420 (NH), 3370 (NH), 1685 (C=O) 1310 (SO₂), 1190 (SO₂) and 1155 cm⁻¹.

EXAMPLE 6

2-[(Trimethylstannyl)methyl]benzenesulfonamide

To a stirred solution of 2-[(dimethyl)hydroxystannylmethyl]benzenesulfonamide, ester with 2,2,2-trifluoroacetic acid (19.1 mmol) in methylene chloride (150 ml) at room temperature under nitrogen was added trimethylaluminum in toluene (2.0 M, 9.9 ml, 20 mmol) dropwise over ¼ hour. After ¼ hour at room temperature, the reaction mixture was heated to reflux for 16 hours and then cooled to 0°. After the addition of 5% HCl (100 ml), the layers were separated and the aqueous layer was extracted with methylene chloride (2×100 ml). The combined methylene chloride layers were washed with water (2×200 ml) and brine (200 ml), dried (MgSO₄), filtered and concentrated in vacuo. Purification by flash chromatography (SiO₂, hexane/ethyl acetate, 7:3) gave 2-[(trimethylstannyl)methyl]benzenesulfonamide (3.7 g, 58%) as a white powder, m.p. 67°-69°.

NMR (CDCl₃)δ: 0.05 (s, Sn(CH₃)₃); 2.7 (s, ArCH₂); 4.9 (broad, NH₂); 6.9-7.6 (m, Ar—H); and 7.9 (d, Ar—H).

IR (KBr): 3490 (NH), 3440 (NH), 3280, (NH), 3260, 1595, 1565, 1555, 1470, 1440, 1325 (SO₂), 1160 (SO₂), 1080 and 760 cm⁻¹.

By using the methods taught in Equations 1-8 and Examples 1-6 the compounds given in Tables 1-3 can be prepared.

TABLE 1

Structure:

$$\begin{array}{c} R_5 \\ | \\ \text{CHSn}(R_1)_2R_2 \end{array}$$

on a benzene ring with positions 1-6, where position 2 bears the CHSn(R₁)₂R₂ group (with R₅), position 1 bears SO₂NR₃R₄, and X is at position 5.

| R₁ | R₂ | R₃ | R₄ | R₅ | X | m.p.(°C.) |
|---|---|---|---|---|---|---|
| CH₃ | CH₃ | H | H | H | H | 67–69° |
| CH₃ | CH₃ | H | CH₃ | H | H | 59–60° |
| CH₃ | CH₃ | H | C₂H₅ | H | H | |
| CH₃ | CH₃ | H | (CH₂)₂CH₃ | H | H | |
| CH₃ | CH₃ | H | CH(CH₃)₂ | H | H | |
| CH₃ | CH₃ | H | (CH₂)₃CH₃ | H | H | oil (IR 3300, 1320, 1160 cm⁻¹) |
| CH₃ | CH₃ | H | C(CH₃)₃ | H | H | oil (IR 3270, 1310, 1150 cm⁻¹) |
| CH₃ | CH₃ | H | (CH₂)₄CH₃ | H | H | |
| CH₃ | CH₃ | H | (CH₂)₁₁CH₃ | H | H | 59–60° |
| CH₃ | CH₃ | H | CH(CH₃)(CH₂)₁₃CH₃ | H | H | |
| CH₃ | CH₃ | H | (CH₂)₁₉CH₃ | H | H | |
| CH₃ | CH₃ | H | cyclopentyl | H | H | |
| CH₃ | CH₃ | H | cyclohexyl | H | H | |
| CH₃ | CH₃ | H | 2-methoxy-thiophen-5-yl (thiophene–OCH₃) | H | H | |
| CH₃ | CH₃ | H | CH₂OCH₃ | H | H | |
| CH₃ | CH₃ | H | (CH₂)₃OCH₃ | H | H | |
| CH₃ | CH₃ | H | phenyl | H | H | 101–104° |
| CH₃ | CH₃ | H | 4-fluorophenyl | H | H | |
| CH₃ | CH₃ | H | 2-chlorophenyl | H | H | |
| CH₃ | CH₃ | H | 2-methylphenyl | H | H | |
| CH₃ | CH₃ | H | 4-methoxyphenyl | H | H | |
| CH₃ | CH₃ | H | 2-methoxyphenyl | H | H | |
| CH₃ | CH₃ | H | 4-chlorophenyl | H | H | |
| CH₃ | CH₃ | H | —CH₂–phenyl | H | H | 64–67° |
| CH₃ | CH₃ | H | —CH₂–(2-chlorophenyl) | H | H | |
| CH₃ | CH₃ | H | —CH₂–(3-fluorophenyl) | H | H | |

TABLE 1-continued $$\text{X} \underset{5}{\overset{4}{\underset{6}{\bigcirc}}} \overset{3}{\underset{1}{\overset{2-\text{CHSn}(R_1)_2R_2}{\text{SO}_2NR_3R_4}}} \overset{R_5}{}$$

| $R_1$ | $R_2$ | $R_3$ | $R_4$ | $R_5$ | X | m.p.(°C.) |
|---|---|---|---|---|---|---|
| $CH_3$ | $CH_3$ | H | —CH$_2$—⬡—OCH$_3$ | H | H | |
| $CH_3$ | $CH_3$ | H | —CH$_2$—⬡(CH$_3$) | H | H | |
| $CH_3$ | $CH_3$ | H | —CH$_2$—⬡(OCH$_3$) | H | H | |
| $CH_3$ | $CH_3$ | $OCH_3$ | H | H | H | |
| $CH_3$ | $CH_3$ | $OCH_3$ | $CH_3$ | H | H | |
| $CH_3$ | $CH_3$ | $OCH_3$ | $(CH_2)CH_3$ | H | H | |
| $CH_3$ | $CH_3$ | $CH_3$ | $CH_3$ | H | H | 59–61° |
| $CH_3$ | $CH_3$ | $CH_3$ | $C_2H_5$ | H | H | oil (IR 1320, 1155 cm$^{-1}$) |
| $CH_3$ | $CH_3$ | $CH_3$ | $(CH_2)_2CH_3$ | H | H | |
| $CH_3$ | $CH_3$ | $CH_3$ | $(CH_2)_4CH_3$ | H | H | |
| $CH_3$ | $CH_3$ | $CH_3$ | $(CH_2)_9CH_3$ | H | H | |
| $CH_3$ | $CH_3$ | $CH_3$ | $(CH_2)_{18}CH_3$ | H | H | |
| $CH_3$ | $CH_3$ | $C_2H_5$ | $C_2H_5$ | H | H | |
| $CH_3$ | $CH_3$ | $C_2H_5$ | $CH(CH_3)_2$ | H | H | |
| $CH_3$ | $CH_3$ | $C_2H_5$ | $CH_2CH_2CH(CH_3)_2$ | H | H | |
| $CH_3$ | $CH_3$ | $C_2H_5$ | $(CH_2)_9CH_3$ | H | H | |
| $CH_3$ | $CH_3$ | $(CH_2)_2CH_3$ | $(CH_2)_2CH_3$ | H | H | |
| $CH_3$ | $CH_3$ | $(CH_2)_2CH_3$ | $(CH_2)_3CH_3$ | H | H | |
| $CH_3$ | $CH_3$ | $(CH_2)_2CH_3$ | $(CH_2)_9CH_3$ | H | H | |
| $CH_3$ | $CH_3$ | $CH(CH_3)_2$ | $CH(CH_3)_3$ | H | H | |
| $CH_3$ | $CH_3$ | $CH(CH_3)_2$ | $(CH_2)_2CH_3$ | H | H | |
| $CH_3$ | $CH_3$ | $CH(CH_3)_2$ | $(CH_2)_{11}CH_3$ | H | H | |
| $CH_3$ | $CH_3$ | $(CH_2)_3CH_3$ | $(CH_2)_3CH_3$ | H | H | |
| $CH_3$ | $CH_3$ | $(CH_2)_3CH_3$ | $C_2H_5$ | H | H | |
| $CH_3$ | $CH_3$ | $(CH_2)_3CH_3$ | $CH(CH_3)C_2H_5$ | H | H | |
| $CH_3$ | $CH_3$ | $CH_2CH(CH_3)_2$ | $CH_2CH(CH_3)_2$ | H | H | |
| $CH_3$ | $CH_3$ | $CH(CH_3)C_2H_5$ | $CH(CH_3)C_2H_5$ | H | H | |
| $CH_3$ | $CH_3$ | $C(CH_3)_3$ | $C(CH_3)_3$ | H | H | |
| $CH_3$ | $CH_3$ | $(CH_2)_4CH_3$ | $(CH_2)_4CH_3$ | H | H | |
| $CH_3$ | $CH_3$ | $(CH_2)_5CH_3$ | $(CH_2)_5CH_3$ | H | H | oil(IR 1320, 1160 cm$^{-1}$) |
| $CH_3$ | $CH_3$ | $(CH_2)_9CH_3$ | $(CH_2)_9CH_3$ | H | H | |
| $CH_3$ | $CH_3$ | $CH_3$ | cyclohexyl | H | H | |
| $CH_3$ | $CH_3$ | $(CH)_5CH_3$ | cyclohexyl | H | H | |
| $CH_3$ | $CH_3$ | $CH_3$ | $CH_2CH_2OCH_3$ | H | H | |
| $CH_3$ | $CH_3$ | $CH_3$ | —⬡ | H | H | oil(IR 1350, 1160 cm$^{-1}$) |
| $CH_3$ | $CH_3$ | $(CH_2)_5CH_3$ | —⬡ | H | H | |
| $CH_3$ | $CH_3$ | $CH_3$ | —⬡—Cl | H | H | |
| $CH_3$ | $CH_3$ | $(CH_2)_2CH_3$ | —⬡(OCH$_3$) | H | H | |
| $CH_3$ | $CH_3$ | $CH_3$ | —CH$_2$—⬡ | H | H | |
| $CH_3$ | $CH_3$ | $C_2H_5$ | —CH$_2$—⬡ | H | H | |

TABLE 1-continued

[Structure: benzene ring with positions labeled 1-6; position 2 bears CHR₅Sn(R₁)₂R₂; position 1 bears SO₂NR₃R₄; X at positions 4/5]

| R₁ | R₂ | R₃ | R₄ | R₅ | X | m.p.(°C) |
|---|---|---|---|---|---|---|
| CH₃ | CH₃ | (CH₂)₃CH₃ | CH₂–C₆H₄–CH₃ | H | H | |
| CH₃ | CH₃ | cyclopentyl | CH₃ | H | H | |
| CH₃ | CH₃ | cyclopentyl | cyclopentyl | H | H | |
| CH₃ | CH₃ | cyclopentyl | –C₆H₅ | H | H | |
| CH₃ | CH₃ | cyclopentyl | CH₂–C₆H₅ | H | H | |
| CH₃ | CH₃ | cyclohexyl | C₂H₅ | H | H | |
| CH₃ | CH₃ | cyclohexyl | (CH₂)₂CH₃ | H | H | |
| CH₃ | CH₃ | cyclohexyl | cyclohexyl | H | H | |
| CH₃ | CH₃ | cyclohexyl | –C₆H₅ | H | H | |
| CH₃ | CH₃ | CH₂OCH₃ | CH₃ | H | H | |
| CH₃ | CH₃ | CH₂OCH₃ | C₂H₅ | H | H | |
| CH₃ | CH₃ | CH₂OCH₃ | CH₂OCH₃ | H | H | |
| CH₃ | CH₃ | CH₂OCH₃ | –C₆H₅ | H | H | |
| CH₃ | CH₃ | CH₂OCH₃ | CH₂–C₆H₅ | H | H | |
| CH₃ | CH₃ | CH₂CH₂OCH₃ | C₂H₅ | H | H | |
| CH₃ | CH₃ | CH₂CH₂OCH₃ | CH₂CH₂OCH₃ | H | H | |
| CH₃ | CH₃ | –C₆H₅ | –C₆H₅ | H | H | |
| CH₃ | CH₃ | –C₆H₅ | –C₆H₄–CH₃ | H | H | |
| CH₃ | CH₃ | –C₆H₅ | –C₆H₄–Cl (o) | H | H | |
| CH₃ | CH₃ | –C₆H₅ | CH₂–C₆H₅ | H | H | |
| CH₃ | CH₃ | –C₆H₄–Cl (o) | –C₆H₄–Cl (o) | H | H | |
| CH₃ | CH₃ | –C₆H₄–F | –C₆H₄–F | H | H | |
| CH₃ | CH₃ | –C₆H₄–CH₃ | –C₆H₄–CH₃ | H | H | |
| CH₃ | CH₃ | –C₆H₄–OCH₃ | –C₆H₄–OCH₃ | H | H | |

TABLE 1-continued $$\text{X}_5 \underset{1}{\overset{4}{\bigcirc}} \underset{6}{\overset{3}{\underset{2}{\bigcirc}}} \overset{R_5}{\underset{SO_2NR_3R_4}{CHSn(R_1)_2R_2}}$$

| R₁ | R₂ | R₃ | R₄ | R₅ | X | m.p.(°C.) |
|---|---|---|---|---|---|---|
| CH₃ | CH₃ | —(CH₂)₄— (cyclic with N) | | H | H | 74–78° |
| CH₃ | CH₃ | —(CH₂)₅— (cyclic with N) | | H | H | oil(IR 1340, 1160 cm⁻¹) |
| CH₃ | CH₃ | —(CH₂)₆— (cyclic with N) | | H | H | |
| CH₃ | CH₃ | (CH₂CH₂)₂CH—CH₃ (cyclic) | | H | H | |
| CH₃ | CH₃ | [CH(CH₃)—CH₂]₂ (cyclic) | | H | H | |
| CH₃ | CH₃ | —CH₂CH₂—O—CH₂CH₂— (cyclic) | | H | H | 66–69° |
| CH₃ | CH₃ | —CH₂CH(CH₃)—O—CH₂CH(CH₃)— (cyclic) | | H | H | |
| CH₃ | CH₃ | —CH₂CH₂—N(CH₃)—CH₂CH₂— (cyclic) | | H | H | 63–72° |
| CH₃ | CH₃ | —CH₂CH₂—N(CH₂)₂CH₃—CH₂CH₂— (cyclic) | | H | H | |
| CH₃ | CH₃ | —CH₂CH(CH₃)—N(CH₃)—CH₂CH(CH₃)— (cyclic) | | H | H | |
| CH₃ | CH₃ | —CH₂C₆H₅ | —CH₂C₆H₅ | H | H | |
| CH₃ | CH₃ | —CH₂C₆H₄OCH₃ | —CH₂C₆H₄OCH₃ | H | H | |

TABLE 1-continued

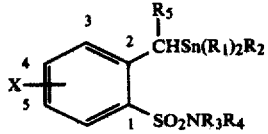

| R₁ | R₂ | R₃ | R₄ | R₅ | X | m.p.(°C.) |
|---|---|---|---|---|---|---|
| CH₃ | CH₃ | —CH₂-(2-CH₃-C₆H₄) | —CH₂-(2-CH₃-C₆H₄) | H | H | |
| CH₃ | CH₃ | H | H | CH₃ | H | |
| CH₃ | CH₃ | H | CH₃ | CH₃ | H | 53-56° |
| CH₃ | CH₃ | CH₃ | CH₃ | CH₃ | H | |
| CH₃ | CH₃ | H | (CH₂)₂CH₃ | CH₃ | H | |
| CH₃ | CH₃ | C(CH₃)₃ | H | CH₃ | H | oil(IR 3280, 1310, 1160 cm⁻¹) |
| CH₃ | CH₃ | H | (CH₂)₁₁CH₃ | CH₃ | H | |
| CH₃ | CH₃ | H | phenyl | CH₃ | H | |
| CH₃ | CH₃ | CH₃ | —CH₂-phenyl | CH₃ | H | |
| CH₃ | CH₃ | phenyl | phenyl | CH₃ | H | |
| CH₃ | CH₃ | —(CH₂)₄— (ring) | | CH₃ | H | oil(IR 1320, 1160 cm⁻¹) |
| CH₃ | CH₃ | —(CH₂)₅— (ring) | | CH₃ | H | |
| CH₃ | CH₃ | —CH₂CH₂—O—CH₂CH₂— (ring) | | CH₃ | H | |
| CH₃ | CH₃ | —CH₂CH₂—N(CH₃)—CH₂CH₂— (ring) | | CH₃ | H | |
| CH₃ | CH₃ | H | H | H | 3-F |
| CH₃ | CH₃ | H | CH₃ | H | 4-Cl |
| CH₃ | CH₃ | CH₃ | CH₃ | H | 5-Cl |
| CH₃ | CH₃ | H | H | H | 3-CH₃ |
| CH₃ | CH₃ | CH₃ | CH₃ | H | 3-CH₃ |
| CH₃ | CH₃ | C(CH₃)₃ | H | H | 4-CH₃ |
| CH₃ | CH₃ | CH₃ | —CH₂-phenyl | H | 4-CH₃ |
| CH₃ | CH₃ | H | H | H | 5-CH₃ |
| CH₃ | CH₃ | CH₃ | H | CH₃ | 6-CH₃ |
| CH₃ | CH₃ | —(CH₂)₅— (ring) | | H | 6-CH₃ |
| CH₃ | CH₃ | H | H | H | 3-OCH₃ |
| CH₃ | CH₃ | CH₃ | CH₃ | CH₃ | 3-OCH₃ |
| CH₃ | CH₃ | H | C(CH₃)₃ | H | 4-OCH₃ |
| CH₃ | CH₃ | —CH₂CH₂—O—CH₂CH₂— (ring) | | H | 5-OCH₃ |
| CH₃ | CH₃ | H | (CH₂)₃CH₃ | H | 6-OCH₃ |
| CH₃ | CH₃ | H | cyclohexyl | CH₃ | 6-OCH₃ |
| C₂H₅ | C₂H₅ | H | H | H | H |

TABLE 1-continued structure: benzene ring with position 1: SO₂NR₃R₄, position 2: CHR₅Sn(R₁)₂R₂, positions 3,4,5,6 on ring, X at position 4/5

| R₁ | R₂ | R₃ | R₄ | R₅ | X | m.p.(°C.) |
|---|---|---|---|---|---|---|
| C₂H₅ | C₂H₅ | CH₃ | H | H | H | oil(IR 3300 1160 cm⁻¹) |
| C₂H₅ | C₂H₅ | CH₃ | CH₃ | H | H | oil(IR 1340 1160 cm⁻¹) |
| C₂H₅ | C₂H₅ | C(CH₃)₃ | H | H | H | |
| C₂H₅ | C₂H₅ | (CH₂)₅CH₃ | (CH₂)₅CH₃ | H | H | |
| C₂H₅ | C₂H₅ | cyclohexyl | H | H | H | |
| C₂H₅ | C₂H₅ | CH₂OCH₃ | CH₂OCH₃ | H | H | |
| C₂H₅ | C₂H₅ | —⟨phenyl⟩ | H | H | H | |
| C₂H₅ | C₂H₅ | H | CH₂—⟨phenyl⟩ | H | H | |
| C₂H₅ | C₂H₅ | CH₂—⟨phenyl⟩ | —CH₂—⟨phenyl⟩ | H | H | |
| C₂H₅ | C₂H₅ | —(CH₂)₄— (R₃ and R₄ joined) | | H | H | |
| C₂H₅ | C₂H₅ | —(CH₂)₅— (R₃ and R₄ joined) | | H | H | |
| C₂H₅ | C₂H₅ | —CH₂CH₂—N(CH₃)—CH₂CH₂— (R₃ and R₄ joined) | | H | 6-F | |
| (CH₂)₂CH₃ | (CH₂)₂CH₃ | H | H | H | H | |
| (CH₂)₂CH₃ | (CH₂)₂CH₃ | H | CH₃ | H | H | |
| (CH₂)₂CH₃ | (CH₂)₂CH₃ | C(CH₃)₃ | H | H | H | oil(IR 3270, 1310, 1150 cm⁻¹) |
| (CH₂)₂CH₃ | (CH₂)₂CH₃ | H | —⟨phenyl⟩ | H | H | |
| (CH₂)₂CH₃ | (CH₂)₂CH₃ | —CH₂—⟨phenyl⟩ | —CH₂—⟨phenyl⟩ | H | H | |
| (CH₂)₂CH₃ | (CH₂)₂CH₃ | —(CH₂)₅— (R₃ and R₄ joined) | | H | H | |
| (CH₂)₂CH₃ | (CH₂)₂CH₃ | —CH₂CH₂—O—CH₂CH₂— (R₃ and R₄ joined) | | H | H | |
| CH(CH₃)₂ | CH(CH₃)₂ | H | H | H | H | |
| CH(CH₃)₂ | CH(CH₃)₂ | CH₃ | CH₃ | H | H | |
| CH(CH₃)₂ | CH(CH₃)₂ | C(CH₃)₃ | H | H | H | |
| CH(CH₃)₂ | CH(CH₃)₂ | —⟨phenyl⟩ | —⟨phenyl⟩ | H | H | |
| CH(CH₃)₂ | CH(CH₃)₂ | CH₂—⟨phenyl⟩ | H | H | H | |

TABLE 1-continued

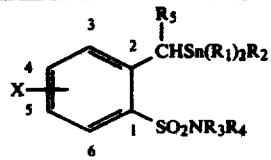

| R₁ | R₂ | R₃ | R₄ | R₅ | X | m.p.(°C) |
|---|---|---|---|---|---|---|
| CH(CH₃)₂ | CH(CH₃)₂ |  | —CH₂CH₂—N(CH₃)—CH₂CH₂— | H | H |  |
| CH₃ | C₂H₅ | H | H | H | H |  |
| CH₃ | C₂H₅ | CH₃ | CH₃ | H | H |  |
| CH₃ | C₂H₅ | (CH₂)₉CH₃ | (CH₂)₉CH₃ | H | H |  |
| CH₃ | C₂H₅ | cyclopentyl | H | H | H |  |
| CH₃ | C₂H₅ | phenyl | phenyl | H | H |  |
| CH₃ | C₂H₅ | —CH₂-phenyl | H | H | H |  |
| CH₃ | C₂H₅ | —(CH₂)₄— |  | H | H |  |
| CH₃ | C₂H₅ | —CH₂CH₂—N(CH₃)—CH₂CH₂— |  | H | H |  |
| CH₃ | (CH₂)₂CH₃ | H | H | H | H |  |
| CH₃ | (CH₂)₂CH₃ | CH₃ | CH₃ | H | H |  |
| CH₃ | (CH₂)₂CH₃ | CH₃ | phenyl | H | H |  |
| CH₃ | (CH₂)₂CH₃ | CH₂-phenyl | CH₂-phenyl | H | H |  |
| CH₃ | CH(CH₃)₂ | H | H | H | H |  |
| CH₃ | CH(CH₃)₂ | CH₃ | CH₃ | H | H |  |
| C₂H₅ | CH₃ | H | H | H | H |  |
| C₂H₅ | CH₃ | CH₂-phenyl | CH₃ | H | H |  |
| C₂H₅ | (CH₂)₂CH₃ | H | H | H | H |  |
| C₂H₅ | (CH₂)₂CH₃ | CH₃ | CH₃ | H | H |  |
| C₂H₅ | CH(CH₃)₂ | H | H | H | H |  |
| C₂H₅ | CH(CH₃)₂ | (CH₂)₁₉CH₃ | H | H | H |  |
| (CH₂)₂CH₃ | CH₃ | H | H | H | H |  |
| (CH₂)₂CH₃ | CH₃ | CH₃ | CH₃ | H | H |  |
| (CH₂)₂CH₃ | C₂H₅ | H | H | H | H |  |
| (CH₂)₂CH₃ | C₂H₅ | C₂H₅ | C₂H₅ | H | H |  |
| CH(CH₃)₂ | CH₃ | H | H | H | H |  |
| CH(CH₃)₂ | (CH₂)₂CH₃ | CH₃ | CH₃ | H | H |  |

TABLE 2

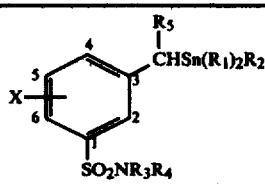

| R₁ | R₂ | R₃ | R₄ | R₅ | X | m.p. (°C) |
|---|---|---|---|---|---|---|
| CH₃ | CH₃ | H | H | H | H |  |
| CH₃ | CH₃ | H | CH₃ | H | H |  |
| CH₃ | CH₃ | H | C₂H₅ | H | H |  |

TABLE 2-continued

Structure: X at position 5/6 of benzene ring; position 3 bears CHR$_5$-Sn(R$_1$)$_2$R$_2$; position 1 bears SO$_2$NR$_3$R$_4$.

| R$_1$ | R$_2$ | R$_3$ | R$_4$ | R$_5$ | X | m.p. (°C.) |
|---|---|---|---|---|---|---|
| CH$_3$ | CH$_3$ | H | (CH$_2$)$_2$CH$_3$ | H | H | |
| CH$_3$ | CH$_3$ | H | CH(CH$_3$)$_2$ | H | H | |
| CH$_3$ | CH$_3$ | H | (CH$_2$)$_3$CH$_3$ | H | H | |
| CH$_3$ | CH$_3$ | H | C(CH$_3$)$_3$ | H | H | |
| CH$_3$ | CH$_3$ | H | (CH$_2$)$_4$CH$_3$ | H | H | |
| CH$_3$ | CH$_3$ | H | (CH$_2$)$_9$CH$_3$ | H | H | |
| CH$_3$ | CH$_3$ | H | CH(C$_2$H$_5$)(CH$_2$)$_{10}$CH$_3$ | H | H | |
| CH$_3$ | CH$_3$ | H | (CH$_2$)$_{19}$CH$_3$ | H | H | |
| CH$_3$ | CH$_3$ | H | cyclopentyl | H | H | |
| CH$_3$ | CH$_3$ | H | cyclohexyl | H | H | |
| CH$_3$ | CH$_3$ | H | 2-methyl-tetrahydrothiopyranyl | H | H | |
| CH$_3$ | CH$_3$ | H | CH$_2$OCH$_3$ | H | H | |
| CH$_3$ | CH$_3$ | H | (CH$_2$)$_3$OCH$_3$ | H | H | |
| CH$_3$ | CH$_3$ | H | phenyl | H | H | |
| CH$_3$ | CH$_3$ | H | 4-fluorophenyl | H | H | |
| CH$_3$ | CH$_3$ | H | 2-chlorophenyl | H | H | |
| CH$_3$ | CH$_3$ | H | 2-methylphenyl | H | H | |
| CH$_3$ | CH$_3$ | H | 4-methoxyphenyl | H | H | |
| CH$_3$ | CH$_3$ | H | 4-chlorophenyl | H | H | |
| CH$_3$ | CH$_3$ | H | —CH$_2$—phenyl | H | H | |
| CH$_3$ | CH$_3$ | H | —CH$_2$—(2-chlorophenyl) | H | H | |
| CH$_3$ | CH$_3$ | H | —CH$_2$—(2-fluorophenyl) | H | H | |
| CH$_3$ | CH$_3$ | H | —CH$_2$—(4-methoxyphenyl) | H | H | |
| CH$_3$ | CH$_3$ | H | —CH$_2$—(2-methylphenyl) | H | H | |
| CH$_3$ | CH$_3$ | OCH$_3$ | H | H | H | |

TABLE 2-continued

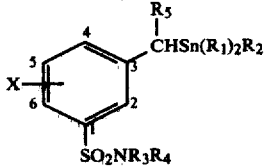

| R₁ | R₂ | R₃ | R₄ | R₅ | X | m.p. (°C.) |
|---|---|---|---|---|---|---|
| CH₃ | CH₃ | OCH₃ | CH₃ | H | H | |
| CH₃ | CH₃ | OCH₃ | (CH)₂CH₃ | H | H | |
| CH₃ | CH₃ | CH₃ | CH₃ | H | H | 74–80° |
| CH₃ | CH₃ | CH₃ | C₂H₅ | H | H | |
| CH₃ | CH₃ | CH₃ | (CH₂)₂CH₃ | H | H | |
| CH₃ | CH₃ | CH₃ | (CH₂)₄CH₃ | H | H | |
| CH₃ | CH₃ | CH₃ | (CH₂)₁₈CH₃ | H | H | |
| CH₃ | CH₃ | C₂H₅ | C₂H₅ | H | H | |
| CH₃ | CH₃ | C₂H₅ | CH(CH₃)₂ | H | H | |
| CH₃ | CH₃ | C₂H₅ | CH₂CH₂CH(CH₃)₂ | H | H | |
| CH₃ | CH₃ | (CH₂)₂CH₃ | (CH₂)₂CH₃ | H | H | |
| CH₃ | CH₃ | (CH₂)₂CH₃ | (CH₂)₉CH₃ | H | H | |
| CH₃ | CH₃ | CH(CH₃)₂ | CH(CH₃)₃ | H | H | |
| CH₃ | CH₃ | CH(CH₃)₂ | (CH₂)₁₁CH₃ | H | H | |
| CH₃ | CH₃ | (CH₂)₃CH₃ | (CH₂)₃CH₃ | H | H | |
| CH₃ | CH₃ | (CH₂)₃CH₃ | C₂H₅ | H | H | |
| CH₃ | CH₃ | (CH₂)₃CH₃ | CH(CH₃)C₂H₅ | H | H | |
| CH₃ | CH₃ | CH₂CH(CH₃)₂ | CH₂CH(CH₃)₂ | H | H | |
| CH₃ | CH₃ | CH(CH₃)C₂H₅ | CH(CH₃)C₂H₅ | H | H | |
| CH₃ | CH₃ | C(CH₃)₃ | C(CH₃)₃ | H | H | |
| CH₃ | CH₃ | (CH₂)₄CH₃ | (CH₂)₄CH₃ | H | H | |
| CH₃ | CH₃ | (CH₂)₉CH₃ | (CH₂)₉CH₃ | H | H | |
| CH₃ | CH₃ | CH₃ | cyclohexyl | H | H | |
| CH₃ | CH₃ | (CH)₅CH₃ | cyclohexyl | H | H | |
| CH₃ | CH₃ | CH₃ | CH₂CH₂OCH₃ | H | H | |
| CH₃ | CH₃ | CH₃ |  | H | H | |
| CH₃ | CH₃ | (CH₂)₅CH₃ |  | H | H | |
| CH₃ | CH₃ | CH₃ | 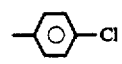 | H | H | |
| CH₃ | CH₃ | (CH₂)₂CH₃ |  | H | H | |
| CH₃ | CH₃ | CH₃ | 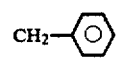 | H | H | |
| CH₃ | CH₃ | (CH₂)₃CH₃ | 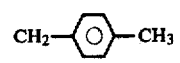 | H | H | |
| CH₃ | CH₃ | cyclopentyl | CH₃ | H | H | |
| CH₃ | CH₃ | cyclopentyl | cyclopentyl | H | H | |
| CH₃ | CH₃ | cyclopentyl | CH₂OCH₃ | H | H | |
| CH₃ | CH₃ | cyclopentyl |  | H | H | |
| CH₃ | CH₃ | cyclopentyl |  | H | H | |
| CH₃ | CH₃ | cyclohexyl | C₂H₅ | H | H | |
| CH₃ | CH₃ | cyclohexyl | (CH₂)₉CH₃ | H | H | |
| CH₃ | CH₃ | cyclohexyl | cyclohexyl | H | H | |
| CH₃ | CH₃ | cyclohexyl |  | H | H | |

TABLE 2-continued

Structure: benzene ring with CHSn(R$_1$)$_2$R$_2$ bearing R$_5$ at position 3, SO$_2$NR$_3$R$_4$ at position 1, and X substituent.

| R$_1$ | R$_2$ | R$_3$ | R$_4$ | R$_5$ | X | m.p. (°C.) |
|---|---|---|---|---|---|---|
| CH$_3$ | CH$_3$ | cyclohexyl | —CH$_2$—C$_6$H$_5$ | H | H | |
| CH$_3$ | CH$_3$ | CH$_2$OCH$_3$ | CH$_3$ | H | H | |
| CH$_3$ | CH$_3$ | CH$_2$OCH$_3$ | CH$_2$OCH$_3$ | H | H | |
| CH$_3$ | CH$_3$ | CH$_2$OCH$_3$ | —C$_6$H$_5$ | H | H | |
| CH$_3$ | CH$_3$ | CH$_2$OCH$_3$ | —CH$_2$—C$_6$H$_5$ | H | H | |
| CH$_3$ | CH$_3$ | CH$_2$CH$_2$OCH$_3$ | C$_2$H$_5$ | H | H | |
| CH$_3$ | CH$_3$ | CH$_2$CH$_2$OCH$_3$ | CH$_2$CH$_2$OCH$_3$ | H | H | |
| CH$_3$ | CH$_3$ | —C$_6$H$_5$ | —C$_6$H$_5$ | H | H | |
| CH$_3$ | CH$_3$ | —C$_6$H$_5$ | 2-Cl-C$_6$H$_4$— | H | H | |
| CH$_3$ | CH$_3$ | —C$_6$H$_5$ | —CH$_2$—C$_6$H$_5$ | H | H | |
| CH$_3$ | CH$_3$ | 2-Cl-C$_6$H$_4$— | 2-Cl-C$_6$H$_4$— | H | H | |
| CH$_3$ | CH$_3$ | 4-F-C$_6$H$_4$— | 4-F-C$_6$H$_4$— | H | H | |
| CH$_3$ | CH$_3$ | 4-CH$_3$-C$_6$H$_4$— | 4-CH$_3$-C$_6$H$_4$— | H | H | |
| CH$_3$ | CH$_3$ | \multicolumn{2}{c}{—(CH$_2$)$_4$—} | H | H | 58–61° |
| CH$_3$ | CH$_3$ | \multicolumn{2}{c}{—(CH$_2$)$_5$—} | H | H | |
| CH$_3$ | CH$_3$ | \multicolumn{2}{c}{—CH$_2$CH$_2$—CH(CH$_3$)—CH$_2$CH$_2$—} | H | H | |
| CH$_3$ | CH$_3$ | \multicolumn{2}{c}{—CH(CH$_3$)—CH$_2$—CH(CH$_3$)—CH$_2$—} | H | H | |
| CH$_3$ | CH$_3$ | \multicolumn{2}{c}{—CH$_2$CH$_2$—O—CH$_2$CH$_2$—} | H | H | 61–64° |

TABLE 2-continued

[Structure: benzene ring with positions 2,3,4,5,6; X at position 5/6; at position 3 is CHR₅Sn(R₁)₂R₂; at position 1 is SO₂NR₃R₄]

| R₁ | R₂ | R₃ | R₄ | R₅ | X | m.p. (°C.) |
|---|---|---|---|---|---|---|
| CH₃ | CH₃ | —CH₂CH(CH₃)—O—CH₂CH(CH₃)— | | H | H | |
| CH₃ | CH₃ | —CH₂—CH₂—N(CH₃)—CH₂—CH₂— | | H | H | |
| CH₃ | CH₃ | —CH₂—CH₂—N(CH₂)₂CH₃—CH₂—CH₂— | | H | H | |
| CH₃ | CH₃ | —CH₂—CH(CH₃)—N(CH₃)—CH₂—CH(CH₃)— | | H | H | |
| CH₃ | CH₃ | —CH₂—C₆H₅ | —C₆H₅ | H | H | |
| CH₃ | CH₃ | —CH₂—C₆H₅ | —CH₂—C₆H₅ | H | H | |
| CH₃ | CH₃ | —CH₂—C₆H₄—OCH₃ | —CH₂—C₆H₄—OCH₃ | H | H | |
| CH₃ | CH₃ | H | H | CH₃ | H | |
| CH₃ | CH₃ | CH₃ | CH₃ | CH₃ | H | |
| CH₃ | CH₃ | C₂H₅ | H | CH₃ | H | |
| CH₃ | CH₃ | H | (CH₂)₂CH₃ | CH₃ | H | |
| CH₃ | CH₃ | C(CH₃)₃ | H | CH₃ | H | |
| CH₃ | CH₃ | H | —C₆H₅ | CH₃ | H | |
| CH₃ | CH₃ | CH₃ | —CH₂—C₆H₅ | CH₃ | H | |
| CH₃ | CH₃ | OCH₃ | CH₃ | CH₃ | H | |
| CH₃ | CH₃ | —C₆H₅ | —C₆H₅ | H | H | |
| CH₃ | CH₃ | —(CH₂)₄— | | CH₃ | H | |

TABLE 2-continued

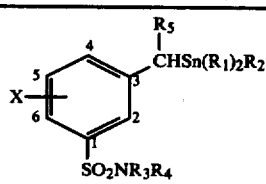

| R₁ | R₂ | R₃ | R₄ | R₅ | X | m.p. (°C.) |
|---|---|---|---|---|---|---|
| CH₃ | CH₃ | | —CH₂CH₂—O—CH₂CH₂— | CH₃ | H | |
| CH₃ | CH₃ | | —CH₂CH₂—N(CH₃)—CH₂CH₂— | CH₃ | H | |
| CH₃ | CH₃ | H | H | H | 2-F | |
| CH₃ | CH₃ | H | CH₃ | H | 4-Cl | |
| CH₃ | CH₃ | CH₃ | CH₃ | H | 5-Cl | |
| CH₃ | CH₃ | H | H | H | 4-CH₃ | |
| CH₃ | CH₃ | H | CH₃ | H | 4-CH₃ | |
| CH₃ | CH₃ | C(CH₃)₃ | H | H | 4-F | |
| CH₃ | CH₃ | CH₃ | CH₂—C₆H₅ | H | 2-Cl | |
| CH₃ | CH₃ | H | H | H | 5-CH₃ | |
| CH₃ | CH₃ | CH₃ | (CH₂)₅CH₃ | H | 5-CH₃ | |
| CH₃ | CH₃ | OCH₃ | CH₃ | H | 5-CH₃ | |
| CH₃ | CH₃ | CH₃ | H | CH₃ | 6-F | |
| CH₃ | CH₃ | —(CH₂)₅— | | H | 6-Cl | |
| CH₃ | CH₃ | CH₃ | CH₃ | CH₃ | 2-OCH₃ | |
| CH₃ | CH₃ | H | C(CH₃)₃ | H | 4-OCH₃ | |
| CH₃ | CH₃ | CH₃ | C₆H₅ | CH₃ | 5-OCH₃ | |
| CH₃ | CH₃ | H | (CH₂)₃CH₃ | H | 6-OCH₃ | |
| CH₃ | CH₃ | H | cyclohexyl | CH₃ | 6-OCH₃ | |
| C₂H₅ | C₂H₅ | H | H | H | H | |
| C₂H₅ | C₂H₅ | CH₃ | CH₃ | H | H | |
| C₂H₅ | C₂H₅ | C(CH₃)₃ | H | H | H | |
| C₂H₅ | C₂H₅ | (CH₂)₅CH₃ | (CH₂)₅CH₃ | H | H | |
| C₂H₅ | C₂H₅ | OCH₃ | CH₃ | H | H | |
| C₂H₅ | C₂H₅ | cyclohexyl | H | H | H | |
| C₂H₅ | C₂H₅ | C₆H₅ | H | H | H | |
| C₂H₅ | C₂H₅ | C₆H₅ | C₆H₅ | H | H | |
| C₂H₅ | C₂H₅ | H | CH₂—C₆H₅ | H | H | |
| C₂H₅ | C₂H₅ | —(CH₂)₄— | | H | H | |
| C₂H₅ | C₂H₅ | —(CH₂)₅— | | CH₃ | H | |

TABLE 2-continued

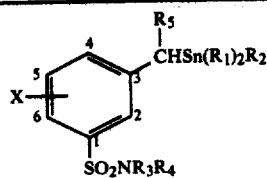

| R₁ | R₂ | R₃ | R₄ | R₅ | X | m.p. (°C.) |
|---|---|---|---|---|---|---|
| C₂H₅ | C₂H₅ | | —CH₂CH₂—O—CH₂CH₂— | H | 2-Cl | |
| C₂H₅ | C₂H₅ | | —CH₂CH₂—N(CH₃)—CH₂CH₂— | H | 6-F | |
| (CH₂)₂CH₃ | (CH₂)₂CH₃ | H | H | H | H | |
| (CH₂)₂CH₃ | (CH₂)₂CH₃ | CH₃ | CH₃ | H | H | |
| (CH₂)₂CH₃ | (CH₂)₂CH₃ | C(CH₃)₃ | H | H | H | |
| (CH₂)₂CH₃ | (CH₂)₂CH₃ | cyclopentyl | H | H | H | |
| (CH₂)₂CH₃ | (CH₂)₂CH₃ | H | phenyl | H | H | |
| (CH₂)₂CH₃ | (CH₂)₂CH₃ | —CH₂—phenyl | —CH₂—phenyl | H | H | |
| (CH₂)₂CH₃ | (CH₂)₂CH₃ | —(CH₂)₅— (cyclic) | | H | H | |
| (CH₂)₂CH₃ | (CH₂)₂CH₃ | —CH₂CH₂—O—CH₂CH₂— | | H | H | |
| CH(CH₃)₂ | CH(CH₃)₂ | H | H | H | H | |
| CH(CH₃)₂ | CH(CH₃)₂ | CH₃ | CH₃ | H | H | |
| CH(CH₃)₂ | CH(CH₃)₂ | C(CH₃)₃ | H | H | H | |
| CH(CH₃)₂ | CH(CH₃)₂ | phenyl | phenyl | H | H | |
| CH(CH₃)₂ | CH(CH₃)₂ | —CH₂CH₂—N(CH₃)—CH₂CH₂— | | H | H | |
| CH₃ | C₂H₅ | H | H | H | H | |
| CH₃ | C₂H₅ | CH₃ | H | H | H | |
| CH₃ | C₂H₅ | CH₃ | CH₃ | H | H | |
| CH₃ | C₂H₅ | cyclopentyl | H | H | H | |
| CH₃ | C₂H₅ | phenyl | phenyl | H | H | |
| CH₃ | C₂H₅ | —CH₂—phenyl | H | H | H | |
| CH₃ | C₂H₅ | —(CH₂)₄— (cyclic) | | H | H | |

TABLE 2-continued

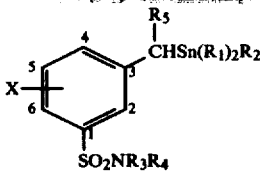

| R₁ | R₂ | R₃ | R₄ | R₅ | X | m.p. (°C.) |
|---|---|---|---|---|---|---|
| CH₃ | C₂H₅ |  | —CH₂CH₂—N(CH₃)—CH₂CH₂— |  | H | H |
| CH₃ | (CH₂)₂CH₃ | H | H | H | H | |
| CH₃ | (CH₂)₂CH₃ | CH₃ | H | H | H | |
| CH₃ | (CH₂)₂CH₃ | (CH₂)₁₉CH₃ | H | H | H | |
| CH₃ | (CH₂)₂CH₃ | CH₃ | phenyl | H | H | |
| CH₃ | (CH₂)₂CH₃ |  | —CH₂CH₂—O—CH₂CH₂— |  | H | H |
| CH₃ | CH(CH₃)₂ | H | H | H | H | |
| CH₃ | CH(CH₃)₂ | CH₃ | CH₃ | H | H | |
| C₂H₅ | CH₃ | H | H | H | H | |
| C₂H₅ | CH₃ | phenyl | phenyl | H | H | |
| C₂H₅ | CH₃ | CH₂-phenyl | CH₃ | H | H | |
| C₂H₅ | CH₃ |  | (CH₂)₆ |  | H | H |
| C₂H₅ | (CH₂)₂CH₃ | H | H | H | H | |
| C₂H₅ | (CH₂)₂CH₃ | CH₃ | CH₃ | H | H | |
| C₂H₅ | (CH₂)₂CH₃ | cyclohexyl | cyclohexyl | H | H | |
| C₂H₅ | CH(CH₃)₂ | (CH₂)₁₉CH₃ | H | H | H | |
| (CH₂)₂CH₃ | CH₃ | H | H | H | H | |
| (CH₂)₂CH₃ | CH₃ | CH₃ | CH₃ | H | H | |
| (CH₂)₂CH₃ | C₂H₅ | H | H | H | H | |
| (CH₂)₂CH₃ | C₂H₅ | C₂H₅ | C₂H₅ | H | H | |
| CH(CH₃)₂ | CH₃ | H | H | H | H | |
| CH(CH₃)₂ | (CH₂)₂CH₃ | CH₃ | CH₃ | H | H | |

TABLE 3

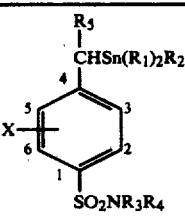

| R₁ | R₂ | R₃ | R₄ | R₅ | X | m.p. (°C.) |
|---|---|---|---|---|---|---|
| CH₃ | CH₃ | H | H | H | H | |
| CH₃ | CH₃ | H | CH₃ | H | H | oil (IR 3400, 1330, and 1160 cm⁻¹) |
| CH₃ | CH₃ | H | C₂H₅ | H | H | |
| CH₃ | CH₃ | H | (CH₂)₂CH₃ | H | H | |
| CH₃ | CH₃ | H | CH(CH₃)₂ | H | H | |
| CH₃ | CH₃ | H | (CH₂)₃CH₃ | H | H | |

TABLE 3-continued

Structure: benzene ring with CHSn(R₁)₂R₂ bearing R₅ at position 4, SO₂NR₃R₄ at position 1, and X substituent.

| R₁ | R₂ | R₃ | R₄ | R₅ | X | m.p. (°C.) |
|---|---|---|---|---|---|---|
| CH₃ | CH₃ | H | C(CH₃)₃ | H | H | |
| CH₃ | CH₃ | H | (CH₂)₄CH₃ | H | H | |
| CH₃ | CH₃ | H | (CH₂)₁₁CH₃ | H | H | |
| CH₃ | CH₃ | H | (CH₂)₁₉CH₃ | H | H | |
| CH₃ | CH₃ | H | cyclopentyl | H | H | |
| CH₃ | CH₃ | H | 2,5-dimethylthiophen-yl | H | H | |
| CH₃ | CH₃ | H | 5-methoxythiophen-yl | H | H | |
| CH₃ | CH₃ | H | CH₂OCH₃ | H | H | |
| CH₃ | CH₃ | H | CH₂CH₂OCH₃ | H | H | |
| CH₃ | CH₃ | H | phenyl | H | H | |
| CH₃ | CH₃ | H | 4-fluorophenyl | H | H | |
| CH₃ | CH₃ | H | 2-methylphenyl | H | H | |
| CH₃ | CH₃ | H | 4-methoxyphenyl | H | H | |
| CH₃ | CH₃ | H | 2-methoxyphenyl | H | H | |
| CH₃ | CH₃ | H | 4-chlorophenyl | H | H | |
| CH₃ | CH₃ | H | —CH₂-phenyl | H | H | |
| CH₃ | CH₃ | H | —CH₂-(2-chlorophenyl) | H | H | |
| CH₃ | CH₃ | H | —CH₂-(2-fluorophenyl) | H | H | |
| CH₃ | CH₃ | H | —CH₂-(4-methylphenyl) | H | H | |
| CH₃ | CH₃ | H | —CH₂-(2-methoxyphenyl) | H | H | |

TABLE 3-continued

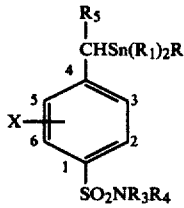

| R₁ | R₂ | R₃ | R₄ | R₅ | X | m.p. (°C.) |
|---|---|---|---|---|---|---|
| CH₃ | CH₃ | OCH₃ | H | H | H | |
| CH₃ | CH₃ | OCH₃ | CH₃ | H | H | |
| CH₃ | CH₃ | OCH₃ | (CH)₂CH₃ | H | H | |
| CH₃ | CH₃ | CH₃ | CH₃ | H | H | 63–66° |
| CH₃ | CH₃ | CH₃ | C₂H₅ | H | H | |
| CH₃ | CH₃ | CH₃ | (CH₂)₂CH₃ | H | H | |
| CH₃ | CH₃ | CH₃ | (CH₂)₉CH₃ | H | H | |
| CH₃ | CH₃ | CH₃ | (CH₂)₁₈CH₃ | H | H | |
| CH₃ | CH₃ | C₂H₅ | C₂H₅ | H | H | |
| CH₃ | CH₃ | C₂H₅ | CH(CH₃)₂ | H | H | |
| CH₃ | CH₃ | C₂H₅ | CH₂CH₂CH(CH₃)₂ | H | H | |
| CH₃ | CH₃ | (CH₂)₂CH₃ | (CH₂)₂CH₃ | H | H | |
| CH₃ | CH₃ | (CH₂)₂CH₃ | (CH₂)₉CH₃ | H | H | |
| CH₃ | CH₃ | CH(CH₃)₂ | CH(CH₃)₃ | H | H | |
| CH₃ | CH₃ | CH(CH₃)₂ | (CH₂)₁₁CH₃ | H | H | |
| CH₃ | CH₃ | (CH₂)₃CH₃ | (CH₂)₃CH₃ | H | H | |
| CH₃ | CH₃ | (CH₂)₃CH₃ | C₂H₅ | H | H | |
| CH₃ | CH₃ | (CH₂)₃CH₃ | CH(CH₃)C₂H₅ | H | H | |
| CH₃ | CH₃ | CH₂CH(CH₃)₂ | CH₂CH(CH₃)₂ | H | H | |
| CH₃ | CH₃ | CH(CH₃)C₂H₅ | CH(CH₃)C₂H₅ | H | H | |
| CH₃ | CH₃ | C(CH₃)₃ | C(CH₃)₃ | H | H | |
| CH₃ | CH₃ | (CH₂)₅CH₃ | (CH₂)₅CH₃ | H | H | oil (IR 1350 and 1165 cm⁻¹) |
| CH₃ | CH₃ | (CH₂)₉CH₃ | (CH₂)₉CH₃ | H | H | |
| CH₃ | CH₃ | CH₃ | cyclohexyl | H | H | |
| CH₃ | CH₃ | (CH)₅CH₃ | cyclohexyl | H | H | |
| CH₃ | CH₃ | CH₃ | CH₂CH₂OCH₃ | H | H | |
| CH₃ | CH₃ | C₂H₅ | (CH₂)₃OC₂H₅ | H | H | |
| CH₃ | CH₃ | CH₃ |  | H | H | 71–75° |
| CH₃ | CH₃ | (CH₂)₅CH₃ |  | H | H | |
| CH₃ | CH₃ | CH₃ | 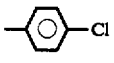 | H | H | |
| CH₃ | CH₃ | (CH₂)₂CH₃ |  | H | H | |
| CH₃ | CH₃ | CH₃ |  | H | H | |
| CH₃ | CH₃ | (CH₂)₃CH₃ | 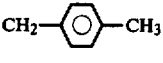 | H | H | |
| CH₃ | CH₃ | cyclopentyl | CH₃ | H | H | oil (IR 1340 and 1160 cm⁻¹) |
| CH₃ | CH₃ | cyclopentyl | cyclopentyl | H | H | |
| CH₃ | CH₃ | cyclopentyl | CH₂OCH₃ | H | H | |
| CH₃ | CH₃ | cyclopentyl |  | H | H | |
| CH₃ | CH₃ | cyclopentyl |  | H | H | |
| CH₃ | CH₃ | cyclohexyl | C₂H₅ | H | H | |

TABLE 3-continued

Structure: phenyl ring with CHSn(R1)2R2 group (with R5) at position 4, SO2NR3R4 at position 1, X at position 5/6.

| R1 | R2 | R3 | R4 | R5 | X | m.p. (°C.) |
|---|---|---|---|---|---|---|
| CH3 | CH3 | cyclohexyl | cyclohexyl | H | H | |
| CH3 | CH3 | cyclohexyl | phenyl | H | H | |
| CH3 | CH3 | cyclohexyl | CH2-phenyl | H | H | |
| CH3 | CH3 | CH2OCH3 | CH3 | H | H | |
| CH3 | CH3 | CH2OCH3 | CH2OCH3 | H | H | |
| CH3 | CH3 | CH2OCH3 | phenyl | H | H | |
| CH3 | CH3 | CH2OCH3 | CH2-phenyl | H | H | |
| CH3 | CH3 | CH2CH2OCH3 | C2H5 | H | H | |
| CH3 | CH3 | CH2CH2OCH3 | CH2CH2OCH3 | H | H | |
| CH3 | CH3 | phenyl | phenyl | H | H | |
| CH3 | CH3 | phenyl | 4-methylphenyl | H | H | |
| CH3 | CH3 | phenyl | CH2-phenyl | H | H | |
| CH3 | CH3 | 2-chlorophenyl | 2-chlorophenyl | H | H | |
| CH3 | CH3 | 4-fluorophenyl | 4-fluorophenyl | H | H | |
| CH3 | CH3 | 4-methoxyphenyl | 4-methoxyphenyl | H | H | |
| CH3 | CH3 | —(CH2)4— (cyclic) | | H | H | 73–76.5° |
| CH3 | CH3 | —(CH2)5— (cyclic) | | H | H | 94–98° |
| CH3 | CH3 | CH2-CH2-CH(CH3)-CH2-CH2 (cyclic with N) | | H | H | |
| CH3 | CH3 | CH(CH3)—CH2 / CH(CH3)—CH2 (cyclic) | | H | H | |

TABLE 3-continued

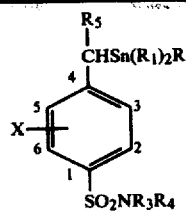

| $R_1$ | $R_2$ | $R_3$ | $R_4$ | $R_5$ | X | m.p. (°C.) |
|---|---|---|---|---|---|---|
| $CH_3$ | $CH_3$ | | $-CH_2CH_2-O-CH_2CH_2-$ (morpholino) | H | H | 118–122° |
| $CH_3$ | $CH_3$ | | $-CH_2CH(CH_3)-O-CH_2CH(CH_3)-$ | H | H | |
| $CH_3$ | $CH_3$ | | $-CH_2-CH_2-N(CH_3)-CH_2-CH_2-$ | H | H | 117–120° |
| $CH_3$ | $CH_3$ | | $-CH_2-CH_2-N(CH_2CH_3)-CH_2-CH_2-$ | H | H | |
| $CH_3$ | $CH_3$ | $-CH_2-C_6H_5$ | $-C_6H_5$ | H | H | |
| $CH_3$ | $CH_3$ | $-CH_2-C_6H_5$ | $-CH_2-C_6H_5$ | H | H | |
| $CH_3$ | $CH_3$ | $-CH_2-C_6H_4-OCH_3$ | $-CH_2-C_6H_4-OCH_3$ | H | H | |
| $CH_3$ | $CH_3$ | H | H | $CH_3$ | H | |
| $CH_3$ | $CH_3$ | H | $CH_3$ | $CH_3$ | H | |
| $CH_3$ | $CH_3$ | $CH_3$ | $CH_3$ | $CH_3$ | H | 79–84° |
| $CH_3$ | $CH_3$ | $C_2H_5$ | H | $CH_3$ | H | |
| $CH_3$ | $CH_3$ | H | $(CH_2)_2CH_3$ | $CH_3$ | H | |
| $CH_3$ | $CH_3$ | $C(CH_3)_3$ | H | $CH_3$ | H | |
| $CH_3$ | $CH_3$ | H | $-C_6H_5$ | $CH_3$ | H | |
| $CH_3$ | $CH_3$ | $CH_3$ | $-CH_2-C_6H_5$ | $CH_3$ | H | |
| $CH_3$ | $CH_3$ | cyclohexyl | $-C_6H_5$ | $CH_3$ | H | |
| $CH_3$ | $CH_3$ | $-C_6H_5$ | $-C_6H_5$ | $CH_3$ | H | |
| $CH_3$ | $CH_3$ | | $-(CH_2)_4-$ | $CH_3$ | H | |

TABLE 3-continued

Structure: Benzene ring with position 4 substituted by CHR₅Sn(R₁)₂R₂, position 1 substituted by SO₂NR₃R₄, and X substituent at positions 2,3,5, or 6.

| R₁ | R₂ | R₃ | R₄ | R₅ | X | m.p. (°C.) |
|---|---|---|---|---|---|---|
| CH₃ | CH₃ | | —CH₂CH₂—O—CH₂CH₂— (morpholino) | CH₃ | H | |
| CH₃ | CH₃ | | —CH₂CH₂—N(CH₃)—CH₂CH₂— (N-methylpiperazino) | CH₃ | H | |
| CH₃ | CH₃ | H | H | H | 3-F | |
| CH₃ | CH₃ | H | CH₃ | H | 2-Cl | |
| CH₃ | CH₃ | C₂H₅ | C₂H₅ | H | 6-Cl | |
| CH₃ | CH₃ | H | H | H | 3-CH₃ | |
| CH₃ | CH₃ | C(CH₃)₃ | H | H | 2-F | |
| CH₃ | CH₃ | H | C₆H₅ | H | 3-Cl | |
| CH₃ | CH₃ | H | H | H | 5-CH₃ | |
| CH₃ | CH₃ | CH₃ | H | H | 5-CH₃ | |
| CH₃ | CH₃ | H | H | H | 6-CH₃ | |
| CH₃ | CH₃ | | (CH₂)₅ | H | 6-CH₃ | |
| CH₃ | CH₃ | H | H | H | 3-OCH₃ | |
| CH₃ | CH₃ | CH₃ | CH₃ | CH₃ | 3-OCH₃ | |
| CH₃ | CH₃ | H | CH₃ | H | 2-OCH₃ | |
| CH₃ | CH₃ | H | C(CH₃)₃ | H | 2-OCH₃ | |
| CH₃ | CH₃ | | —CH₂CH₂—O—CH₂CH₂— | H | 5-OCH₃ | |
| CH₃ | CH₃ | H | (CH₂)₃CH₃ | H | 6-OCH₃ | |
| CH₃ | CH₃ | H | cyclohexyl | CH₃ | 6-OCH₃ | |
| C₂H₅ | C₂H₅ | H | H | H | H | |
| C₂H₅ | C₂H₅ | CH₃ | H | H | H | |
| C₂H₅ | C₂H₅ | CH₃ | CH₃ | H | H | |
| C₂H₅ | C₂H₅ | C(CH₃)₃ | H | H | H | |
| C₂H₅ | C₂H₅ | (CH₂)₅CH₃ | (CH₂)₅CH₃ | H | H | |
| C₂H₅ | C₂H₅ | OCH₃ | CH₃ | H | H | |
| C₂H₅ | C₂H₅ | cyclohexyl | H | H | H | |
| C₂H₅ | C₂H₅ | C₆H₅ | H | H | H | |
| C₂H₅ | C₂H₅ | C₆H₅ | C₆H₅ | H | H | |
| C₂H₅ | C₂H₅ | H | CH₂C₆H₅ | H | H | |
| C₂H₅ | C₂H₅ | CH₂C₆H₅ | —CH₂C₆H₅ | H | H | |

TABLE 3-continued (structure)

$R_5$ — CHSn($R_1$)$_2$$R_2$ at position 4; X at positions 5/6; $SO_2NR_3R_4$ at position 1

| $R_1$ | $R_2$ | $R_3$ | $R_4$ | $R_5$ | X | m.p. (°C.) |
|---|---|---|---|---|---|---|
| $C_2H_5$ | $C_2H_5$ | \-(CH$_2$)$_5$\- | | $CH_3$ | H | |
| $C_2H_5$ | $C_2H_5$ | —CH$_2$CH$_2$—O—CH$_2$CH$_2$— | | H | 3-Cl | |
| $C_2H_5$ | $C_2H_5$ | —CH$_2$CH$_2$—N(CH$_3$)—CH$_2$CH$_2$— | | H | 6-F | |
| (CH$_2$)$_2$CH$_3$ | (CH$_2$)$_2$CH$_3$ | H | H | H | H | |
| (CH$_2$)$_2$CH$_3$ | (CH$_2$)$_2$CH$_3$ | H | CH$_3$ | H | H | |
| (CH$_2$)$_2$CH$_3$ | (CH$_2$)$_2$ch$_3$ | CH$_3$ | CH$_3$ | H | H | |
| (CH$_2$)$_2$CH$_3$ | (CH$_2$)$_2$CH$_3$ | C(CH$_3$)$_3$ | H | H | H | |
| (CH$_2$)$_2$CH$_3$ | (CH$_2$)$_2$CH$_3$ | —CH$_2$Ph | —CH$_2$Ph | H | H | |
| (CH$_2$)$_2$CH$_3$ | (CH$_2$)$_2$CH$_3$ | \-(CH$_2$)$_5$\- | | H | H | |
| (CH$_2$)$_2$CH$_3$ | (CH$_2$)$_2$CH$_3$ | —CH$_2$CH$_2$—O—CH$_2$CH$_2$— | | H | H | |
| CH(CH$_3$)$_2$ | CH(CH$_3$)$_2$ | H | H | H | H | |
| CH(CH$_3$)$_2$ | CH(CH$_3$)$_2$ | H | CH$_3$ | H | H | |
| CH(CH$_3$)$_2$ | CH(CH$_3$)$_2$ | CH$_3$ | CH$_3$ | H | H | |
| CH(CH$_3$)$_2$ | CH(CH$_3$)$_2$ | C(CH$_3$)$_3$ | H | H | H | |
| CH(CH$_3$)$_2$ | CH(CH$_3$)$_2$ | Ph | Ph | H | H | |
| CH(CH$_3$)$_2$ | CH(CH$_3$)$_2$ | CH$_2$Ph | H | H | H | |
| CH(CH$_3$)$_2$ | CH(CH$_3$)$_2$ | —CH$_2$CH$_2$—N(CH$_3$)—CH$_2$CH$_2$— | | H | H | |
| CH$_3$ | C$_2$H$_5$ | H | H | H | H | |
| CH$_3$ | C$_2$H$_5$ | CH$_3$ | H | H | H | |
| CH$_3$ | C$_2$H$_5$ | CH$_3$ | CH$_3$ | H | H | |
| CH$_3$ | C$_2$H$_5$ | (CH$_2$)$_9$CH$_3$ | (CH$_2$)$_9$CH$_3$ | H | H | |
| CH$_3$ | C$_2$H$_5$ | cyclopentyl | H | H | H | |
| CH$_3$ | C$_2$H$_5$ | Ph | Ph | H | H | |
| CH$_3$ | C$_2$H$_5$ | —CH$_2$Ph | H | H | H | |

TABLE 3-continued

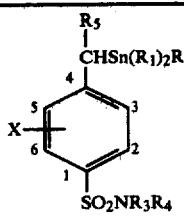

| $R_1$ | $R_2$ | $R_3$ | $R_4$ | $R_5$ | X | m.p. (°C.) |
|---|---|---|---|---|---|---|
| $CH_3$ | $C_2H_5$ | \multicolumn{2}{c|}{$(CH_2)_4$} | H | H | |
| $CH_3$ | $C_2H_5$ | \multicolumn{2}{c|}{$-CH_2CH_2\diagdown NCH_3 / -CH_2CH_2$} | H | H | |
| $CH_3$ | $(CH_2)_2CH_3$ | H | H | H | H | |
| $CH_3$ | $(CH_2)_2CH_3$ | $CH_3$ | H | H | H | |
| $CH_3$ | $(CH_2)_2CH_3$ | $(CH_2)_{19}CH_3$ | H | H | H | |
| $CH_3$ | $(CH_2)_2CH_3$ | $CH_3$ | $-\!\!\langle O\rangle$ | H | H | |
| $CH_3$ | $(CH_2)_2CH_3$ | $CH_2-\!\langle O\rangle$ | $CH_2-\!\langle O\rangle$ | H | H | |
| $CH_3$ | $(CH_2)_2CH_3$ | \multicolumn{2}{c|}{$-CH_2CH_2\diagdown O / -CH_2CH_2$} | H | H | |
| $CH_3$ | $CH(CH_3)_2$ | H | H | H | H | |
| $CH_3$ | $CH(CH_3)_2$ | $CH_3$ | $CH_3$ | H | H | |
| $C_2H_5$ | $CH_3$ | H | H | H | H | |
| $C_2H_5$ | $CH_3$ | $-\!\langle O\rangle$ | $-\!\langle O\rangle$ | H | H | |
| $C_2H_5$ | $CH_3$ | \multicolumn{2}{c|}{$(CH_2)_6$} | H | H | |
| $C_2H_5$ | $(CH_2)_2CH_3$ | H | H | H | H | |
| $C_2H_5$ | $(CH_2)_2CH_3$ | cyclohexyl | cyclohexyl | H | H | |
| $C_2H_5$ | $CH(CH_3)_2$ | $(CH_2)_{19}CH_3$ | H | H | H | |
| $(CH_2)_2CH_3$ | $CH_3$ | H | H | H | H | |
| $(CH_2)_2CH_3$ | $CH_3$ | $CH_3$ | $CH_3$ | H | H | |
| $(CH_2)_2CH_3$ | $C_2H_5$ | $C_2H_5$ | $C_2H_5$ | H | H | |
| $(CH_2)_2CH_3$ | $CH(CH_3)_2$ | H | H | H | H | |
| $CH(CH_3)_2$ | $CH_3$ | H | H | H | H | |
| $CH(CH_3)_2$ | $(CH_2)_2CH_3$ | $CH_3$ | $CH_3$ | H | H | |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they can contain these ingredients in the following approximate proportions:

TABLE 4

| | Active Ingredient | Weight Percent* | |
|---|---|---|---|
| | | Diluent(s) | Surfactant(s) |
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength | 90–99 | 0–10 | 0–2 |

TABLE 4-continued

| | Active Ingredient | Weight Percent* Diluent(s) | Surfactant(s) |
|---|---|---|---|
| Compositions | | | |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, New York, 1973, pp. 8-57ff.

For further information regarding the art of formulation, see for example:
- J. B. Buchanan, U.S. Pat. No. 3,576,834, Apr. 27, 1971, Col. 5, Line 36 through Col. 7, line 70 and Examples 1-4, 17, 106 and 123-140;
- R. R. Shaffer, U.S. Pat. No. 3,560,616, Feb. 2, 1971, Col. 3, Line 48 through Col. 7, Line 26 and Examples 3-9 and 11-18; and
- E. Somers, "Formulation", Chapter 6 in Torgeson, "Fungicides", Vol. I, Academic Press, New York, 1967.

EXAMPLE 7

High Strength Concentrate

N-(1,1-dimethylethyl)-2-(trimethylstannyl)benzenesulfonamide: 98.5%
silica aerogel: 0.5%
synthetic amorphous fine silica: 1.0%

The ingredients are blended and ground in a hammermill to produce a high strength concentrate essentially all passing a U.S.S. No. 50 sieve (0.3 mm openings). This material may then be formulated in a variety of ways.

EXAMPLE 8

Emulsifiable Concentrate

N-butyl-2-[(trimethylstannyl)methyl]benzenesulfonamide: 20%
chlorobenzene: 74%
sorbitan monostearate and polyoxyethylene condensates thereof: 6%

The ingredients are combined and stirred to produce a solution which can be emulsified in water for application.

EXAMPLE 9

Wettable Powder

N-phenyl-2-[(trimethylstannyl)methyl]benzenesulfonamide: 40%
dioctyl sodium sulfosuccinate: 1.5%
sodium ligninsulfonate: 3%
low viscosity methyl cellulose: 1.5%
attapulgite: 54%

The ingredients are thoroughly blended, passed through an air mill to produce an average particle size under 15 microns, reblended and sifted through a U.S.S. No. 50 sieve (0.3 mm opening) before packaging.

EXAMPLE 10

Oil Suspension

1-[2-[(trimethylstannyl)methyl]phenylsulfonyl]pyrrolidine: 25%
polyoxyethylene sorbitol hexaoleate: 5%
highly aliphatic hydrocarbon oil: 70%

The ingredients are ground together in a sand mill until the solid particles have been reduced to under about 5 microns. The resulting suspension may be applied directly, but preferably after being extended with oils or emulsified in water.

EXAMPLE 11

Emulsifiable Concentrate

N,N-dihexyl-2-[(trimethylstannyl)methyl]benzenesulfonamide: 30%
blend of oil soluble sulfonates and polyoxyethylene ethers: 4%
xylene: 66%

The ingredients are combined and stirred with gentle warming to speed solution. A fine screen filter is included in the packaging operation to insure the absence of any extraneous undissolved material in the product.

All compounds of the invention may be formulated in this same manner.

EXAMPLE 12

Granule

2-[(trimethylstannyl)methyl]benzenesulfonamide: 10%
attapulgite granules (low volative matter, 0.71/0.30 mm; U.S.S. No. 25-50 sieves): 90%

The active ingredient is warmed to approximately 90° C. and sprayed upon dedusted and pre-warmed attapulgite granules in a double cone blender. The granules are then allowed to cool and are packaged.

Insecticidal Sulfonamides

Use

Compounds of Formula 1 have insecticidal activity on major agricultural, public health and household pests. The examples demonstrate the control efficacy of representative compounds of Formula 1, which are listed in Table 1.

These compounds have a wide spectrum of insecticidal activity, controlling economically significant pest species in the insect orders Lepidoptera, Homoptera, Diptera, and Coleoptera and species of the arachnid order Acari (suborder Prostigmata). More specifically, arthropods controlled by these compounds include, but are not limited to: the southern armyworm (*Spodoptera eridania*), fall armyworm (*Spodoptera frugiparda*), tobacco budworm (*Heliothis virescens*), boll weevil (*Anthonamous grandis*), housefly (*Musca domestica*), aster leaf hopper (*Macrosteles fascifrous*), black bean aphid (*Aphis fabae*), southern corn rootworm (*Diabrotica undecimpunctata*) and two-spotted spider mite (*Tetranychus urticae*).

Control is achieved through application of one or more of the compounds of Formula I to the area to be protected, to the pests themselves, and/or the locus of infestation. The usual methods of application to agricultural crops, using compounds of this invention, are by foliar application, soil applications, or applications to those plant parts which are to be protected. Applications, however, are not limited to these methods. The rate of application required for effective control is dependent upon both biological factors, e.g., the pest species, its life stage, size, and location, and upon non-biological factors, e.g., weather conditions (temperature, rainfall, humidity, etc.), time of year, application method, crop (plant growth habit and characteristics), and agronomic factors (crop spacing, soil type, etc.). In general, application rates of 0.01 to 8 kg/ha may be required for pest control in agriculture, the rates being dependent upon the above listed biological and non-biological factors. However, rates of 0.05 to 2 kg/ha will, under normal circumstances result in effective control. Rates of 0.10 to 1.5 kg/ha will normally be used in large scale field operations.

Compounds of Formula I can be mixed with insecticides, fungicides, nematicides, bactericides, acaricides, and/or other biologically active compounds, in order to achieve effective control with a minimum of input of material, time and effort. The mixture ratio for each part by weight of compounds of this invention with the above listed biologically active chemicals may vary from 0.20 to 5.00 parts by weight. The following list consists of a few select examples of chemicals presently employed in the above listed control classes. The mixture composition, however, is not to be construed as being limited solely to the various possible combinations of those compounds.

Insecticides 3-hydroxy-N-methylcrotonamide dimethylphosphate ester (Azodrin ®)
methylcarbamic acid, ester with 2,3-dihydro-2,2-dimethyl-7-benzofuranol (Furadan ®)
O-[2,4,5-trichloro-α-(chloromethyl)benzyl]phosphoric acid, O', O'-dimethyl ester (Gardona ®)
2-mercaptosuccinic acid, diethyl ester S-ester with thionophosphoric acid, dimethyl ester (Malathion ®)
phosphorothioic acid, O,O-dimethyl, O-p-nitrophenyl ester (methyl parathion)
methylcarbamic acid, ester with α-naphthol (Sevin ®)
methyl O-(methylcarbamoyl)thiolacetohydroxamate (methomyl)
N'-(4-chloro-o-tolyl)-N,N-dimethylformamidine (Galecron ®)
O,O-diethyl-O-(2-isopropyl-4-methyl-6-pyrimidyl)-phosphorothioate (Diazinon ®)
octachlorocamphene (toxaphene)
O-ethyl O-p-nitrophenyl phenylphosphonothioate (EPN)
(S)-α-cyano-m-phenoxybenzyl(1R, 3R)-3-(2,2-dibromovinyl)-2,2-dimethylcyclopropane-carboxylate (Decis ®)
Methyl N',N'-dimethyl-N-[(methylcarbamoyl)oxy]-1-thiooxamimidate (oxamyl)
cyano(3-phenoxyphenyl)-methyl-4-chloro-α-(1-methylethyl)benzeneacetate (Pydrin ®)
(3-phenoxyphenyl)methyl(-1)-cis,trans-3-(2,2-dichloroethenyl)-2,2-dimethylcyclopropanecarboxylate (Ambush ®)
O-ethyl-S-(p-chlorophenyl)ethylphosphonodithioate (Curacron ®)
phosphorothiolothionic acid, O-ethyl-O-[4-(methylthio)phenyl]-S-n-propyl ester (Bolstar ®)

Fungicides methyl 2-benzimidazolecarbamate (carbendazim)
tetramethyl thiuram disulfide (thiuram)
n-dodecylguanidine acetate (dodine)
manganese ethylenebisdithiocarbamate (maneb)
1,4-dichloro-2,5-dimethoxybenzene (chloroneb)
methyl 1-(butylcarbamoyl)-2-benzimidazolecarbamate (benomyl)
1-[2-(2,4-dichlorophenyl)-4-propyl-1,3-dioloxan-2-yl-methyl]-1H-1,2,4-triazole (propaconazole)
2-cyano-N-ethylcarbamoyl-2-methoxyiminoacetamide (Curzate ®)
1-(4-chlorophenoxy)-3,3-dimethyl-1-(1H-1,2,4-triazol-1-yl)-2-butanone (triadimefon)
N-trichloromethylthiotetrahydrophthalimide (captan)
N-trichloromethylthiophthalimide (folpet)

Nematicides

S-methyl 1-(dimethylcarbamoyl)-N-(methylcarbamoyloxy)thioformimidate
S-methyl 1-carbamoyl-N-(methylcarbamoyloxy)thioformimidate
N-isopropylphosphoramidic acid, O-ethyl-O'-[4-(methylthio)-m-tolyl]diester (Nemacur ®)

Bactericides tribasic copper sulfate
streptomycin sulfate

Acaricides senecioic acid, ester with 2-sec-butyl-4,6-dinitrophenol (Morocide ®)
6-methyl-1,3-dithiolo[2,3-b]quinonolin-2-one (Morestan ®)
ethyl 4,4'-dichlorobenzilate (Chlorobenzilate ®)
1,1-bis(p-chlorophenyl)-2,2,2-trichloroethane (Kelthane ®)
bis(pentachloro-2,4-cyclopentadien-1-yl) (Pentac ®)
tricyclohexyl tinhydroxide (Plictran ®)

TABLE 5

| Compound Number | Compound |
|---|---|
| 1 | 2-[(trimethylstannyl)methyl] benzenesulfonamide |
| 2 | N—methyl-2-[(trimethylstannyl)methyl] benzenesulfonamide |

TABLE 5-continued

| Compound Number | Compound |
|---|---|
| 3 | N,N—dimethyl-2-[(trimethylstannyl)methyl]-benzenesulfonamide |
| 4 | N—butyl-2-[(trimethylstannyl)methyl] benzenesulfonamide |
| 5 | N—(1,1-dimethylethyl)-2-[(trimethylstannyl)methyl] benzenesulfonamide |
| 6 | N—ethyl-N—methyl-2-[(trimethylstannyl)methyl]-benzenesulfonamide |
| 7 | N,N—dihexyl-2-[(trimethylstannyl)methyl]-benzenesulfonamide |
| 8 | N—dodecyl-2-[(trimethylstannyl)methyl] benzenesulfonamide |
| 9 | N—phenyl-2-[(trimethylstannyl)methyl] benzenesulfonamide |
| 10 | 4-[2-[(trimethylstannyl)methyl] phenylsulfonyl] morpholine |
| 11 | 1-[2-[(trimethylstannyl)methyl)phenylsulfonyl] pyrrolidine |

EXAMPLE 13

Single excised red kidney bean leaves were sprayed with a 2000 ppm acetone solution of the compounds listed below using an atomizing nozzle at 30 psi. The treated leaf was then place into a 10 cm plastic petri dish containing a moist 9 cm filter paper and five (5) third instar southern armyworm larvae. Test units were maintained in the laboratory at 27°±1° C. and 48%±5% relative humidity (RH). Mortality and feeding inhibition evaluations were made at 72 hours after treatment.

| Compound Numbers | % Control (72 hrs) |
|---|---|
| 1 | 100 |
| 2 | 100 |
| 3 | 100 |
| 4 | 100 |
| 5 | 100 |
| 7 | 100 |

EXAMPLE 14

Activity against fall armyworm was demonstrated using a test unit consisting of an 8 oz. plastic cup supplied with armyworm diet. Ten (10) third instar larvae were sprayed directly with a 75:25, acetone:distilled water solution of the compounds listed below at a rate of 0.5 lb. a.i./acre using a flat fan hydraulic nozzle. The test cups were covered upon exiting the sprayer and held at 27°±1° C. and 48%±5% RH for mortality evaluations at 24, 48 and 72 hours after treatment.

| Compound Numbers | % control (72 hrs) |
|---|---|
| 6 | 100 |
| 8 | 100 |
| 9 | 100 |
| 10 | 100 |
| 11 | 100 |

EXAMPLE 15

On the day of testing large cloths on which *Heliothis virescens* eggs had been deposited were collected. These cloths were cut into small pieces, small enough to fit into a 35×15 mm petri dish, each with 20–30 eggs. The small egg cloths were held in the petri dishes with a drop of honey. The dish was uncovered prior to passing under the atomizing nozzle, driving the 2000 ppm acetone solution with 30 psi air pressure. The dishes were recovered upon exiting the sprayer and held in the laboratory at 27°±1° C. and 48%±5% RH for 72 hours before being evaluated for ovicidal activity.

| Compound Numbers | % control (72 hrs) |
|---|---|
| 1 | 100 |
| 2 | 100 |
| 3 | 100 |
| 5 | 100 |
| 7 | 100 |

Tests run with compound 4 using the same procedures as above resulted in no control of *Heliothis virescens*. It is believed that compound 4 would provide control at higher concentrations or under modified conditions. Compound 4 has been found to effectively control southern armyworm larvae (Example 13) and housefly larvae (Example 20).

EXAMPLE 16

Activity against tobacco budworm was demonstrated using a test unit consisting of 8 oz. plastic cups supplied with budworm diet. Ten (10) third instar larvae were sprayed directly with a 75:25 acetone:distilled water solution of the compounds listed below at a rate of 0.5 lb. a.i./acre using a flat fan hydraulic nozzle. The test cups were covered upon exiting the sprayer and held at 27°±1° C. and 48%±5% RH for mortality evaluations at 24, 48 and 72 hours after treatment

| Compound Numbers | % control (72 hrs) |
|---|---|
| 6 | 100 |
| 8 | 100 |
| 9 | 100 |
| 10 | 100 |
| 11 | 100 |

EXAMPLE 17

Activity as a tobacco budworm ovicide was demonstrated using a test unit consisting of an egg cloth having 15–25 eggs secured to the lid of a 35×15 mm plastic petri dish. The eggs were sprayed directly with a 75:25 acetone:distilled water solution of the compounds listed below at a rate of 0.5 lb. a.i./acre using a flat fan hydraulic nozzle. Test units were capped after drying. Budworm diet was added after 24 hours, and the test units were held at 27°±1° C. and 48%±5% RH for evaluation at 72 hours after treatment.

| Compound Numbers | % control (72 hrs) |
|---|---|
| 6 | 100 |
| 8 | 100 |
| 9 | 100 |
| 10 | 100 |
| 11 | 100 |

EXAMPLE 18

Five (5) adult boll weevils were placed in 9 oz. plastic cups having the inner lip greased with a petroleum jelly/mineral oil mixture to prevent escape of the insects prior to and during spraying. The weevils were sprayed directly with a 2000 ppm solution of the compounds listed below, using a hydraulic nozzle at a rate of 0.5 lb. a.i./acre. After treatment the cups were capped with a plastic lid. Weevils were held in the laboratory at 27°±1° C. and 48%±5% RH, and mortality evaluations were made at 48 hours after treatment.

| Compound Numbers | % control (48 hrs) |
|---|---|
| 6 | 100 |
| 8 | 100 |
| 10 | 100 |

Tests run with compound 5 using essentially the same procedures as above with the exception that 8 oz. glass jars were substituted for the 9 oz. plastic cups resulted in no control of boll weevils. It is believed that compound 5 would provide control at higher concentrations or under modified conditions. Compound 5 has been found to effectively control armyworm larvae (Example 13) and houseflies (Example 19).

EXAMPLE 19

Nine (9) oz. plastic cup were sprayed with a 2000 ppm acetone solution of the compounds listed below using an atomizing nozzle driven by 30 psi air pressure. After treatment, a cotton wick saturated with a 10% sugar solution was added to each cup as a water and food source for the insects. Fifteen to twenty adult houseflies were $CO_2$ anesthetized to facilitate collection and added to each test cup, after which the cups were capped and held at 27°±1° C. and 48%±5% RH. Mortality evaluations were made after 24 hours.

| Compound Numbers | % Control (24 hrs) |
|---|---|
| 1 | 100 |
| 2 | 100 |
| 3 | 100 |
| 5 | 100 |

Tests run with compounds 4 and 7 using the same procedures as above resulted in no control of adult houseflies. It is believed that both compound 4 and 7 would provide control at higher concentrations or under modified conditions. Compounds 4 and 7 have been found to effectively control southern armyworm larvae (Example 13).

EXAMPLE 20

Nine (9) oz. plastic cups containing larvae fly culture media were sprayed with a 2000 ppm acetone solution of the compounds listed below using an atomizing nozzle driven by 30 psi air pressure. After treatment, 10 housefly larvae were added to each cup. The cups were capped with paper toweling held in place with elastic bands. The test cups were held at 27°±1° C. and 48%±5% RH for 14 days, at which time they were examined for evidence of developmental anomalies or arrest.

| Compound Numbers | % Control |
|---|---|
| 3 | 70 |
| 4 | 100 |
| 5 | 60 |

Tests run with compounds 1, 2, and 7 using the same procedures as above resulted in no control of housefly larvae. It is believed that compounds 1, 2, and 7 would provide control at higher concentrations or under modified conditions. Compounds 1, 2, and 7 have been found to effectively control *Heliothis virescens* (Example 15).

EXAMPLE 21

Nine (9) oz. plastic cups were sprayed with the compounds listed below at a rate of 0.5 lb. a.i./acre in a 75:25 acetone:distilled water solution using a hydraulic flat fan nozzle. After treatment, a cotton wick saturated with a 10% sugar solution was added to each cup as a source of water and food for the insects. Fifteen to twenty adult houseflies were $CO_2$ anesthetized to facilitate collection and added to each test cup, after which the cups were capped and held at 27°±1° C. and 48%±5% RH. Mortality evaluations were made after 24 hours.

| Compound Numbers | % Control |
|---|---|
| 6 | 100 |
| 8 | 32 |
| 9 | 100 |
| 10 | 100 |
| 11 | 100 |

EXAMPLE 22

Activity against aster leafhoppers was demonstrated using test units consisting of a 12 oz. plastic cup containing 4-8 rye seedlings growing in a 1-inch layer of sterilized soil. Rye seedlings were six days old when sprayed with a 2000 ppm acetone solution of the compounds listed below. An atomizing nozzle driven at 30 psi air pressure was used. After treatment, the cups were capped with a plastic lid. A vacuum aspirator was used to collect adult leafhoppers from the culture cages and 10-15 leafhoppers were placed in each test cup and held at 27°±1° C. and 48%±5% RH. Mortality evaluations were made at 24 and 48 hours after treatment.

| Compound Numbers | % Control (48 hrs) |
|---|---|
| 1 | 100 |
| 5 | 100 |

EXAMPLE 23

Activity against aster leafhoppers was determined using test units consisting of a 12 oz. plastic cup containing 4-8 oat seedlings growing in a 1-inch layer of sterilized soil. The seedlings were 6 days old when sprayed with a 75:25 acetone:distilled water solution of the compounds listed below at a rate of 0.5 lb. a.i./acre. A flat fan hydraulic nozzle was used. After treatment the cups were capped with a plastic lid. A vacuum aspirator was used to collect adult leafhoppers from the culture cages and 10-15 leafhoppers were placed in each test cup and held at 27°±1° C. and 48%±5% RH. Mortality evaluations were made at 48 hours after treatment.

| Compound Numbers | % Control (48 hrs) |
|---|---|
| 6 | 100 |
| 8 | 100 |
| 9 | 100 |
| 10 | 100 |
| 11 | 100 |

EXAMPLE 24

The stem of a single, aphid-infested nasturtium leaf was cut and placed in a 1-dram glass vial filled with a 10% sugar solution. The vial lid had a hole in it to facilitate passage of the stem through the lid. Leaves with 20-30 aphids were chosen for testing. The infested leaves were subsequently removed from the vials and inverted, thereby exposing the aphids to a direct spray, and held in place by an insect pin protruding up from the test rack. The aphids were sprayed with a 2000 ppm acetone solution of the compounds listed below using an atomizing nozzle driven by 30 psi air pressure. Test leaves were then returned to the vials and held in a covered rack at 27°±1° C. and 48%±5% RH until mortality evaluations were made, 48 hours after treatment.

| Compound Numbers | % Control (48 hrs) |
|---|---|
| 1 | 100 |
| 2 | 100 |
| 3 | 100 |
| 4 | 100 |
| 7 | 95 |

Tests run with compound 5 using the same procedure as above resulted in no control of aphids. It is believed that compound 5 would provide control at higher concentrations or under modified conditions. Compound 5 has been found to effectively control armyworm larvae (Example 13) and houseflies (Example 19).

EXAMPLE 25

The stem of a single, aphid-infested nasturtium leaf was cut and placed in a 1-dram glass vial filled with a 10% sugar solution. The vial lid had a hole in it to facilitate passage of the stem through the lid. Leaves with 20-30 aphids were chosen for testing. The infested leaves were subsequently removed from the vials and inverted, thereby exposing the aphids to a direct spray, and held in place by an insect pin protruding from the test rack. The aphids were sprayed with a 75:25 acetone:distilled water solution of the compounds listed below at a rate of 0.5 lb. a.i./acre. Test leaves were then returned to the vials and held in a covered rack at 27°±1° C. and 48%±5% RH until mortality evaluations were made, 48 hours after treatment.

| Compound Numbers | % Control (48 hrs) |
|---|---|
| 6 | 100 |
| 8 | 100 |
| 9 | 100 |
| 10 | 100 |
| 11 | 100 |

EXAMPLE 26

Pinto bean leaves were punched to a diameter of approximately 0.75 inches four days prior to infestation with two-spotted spider mites. Mites were transferred from the culture to the uniformly trimmed pinto bean leaves 24 hours prior to testing, thereby allowing the mites to become established. Leaves with 20-30 mites were chosen for testing. The infested leaves were removed from the plant and inverted, thereby exposing the mites to direct spray, and held in place by an insect pin protruding up from the test rack. The mites were sprayed with a 2000 ppm acetone solution of the compounds listed below using an atomizing nozzle driven by 30 psi air pressure. The petiole of the treated, infested leaf was placed in a 1-dram glass vial filled with water. The vials were held in a covered rack at 27°±1° C. and 48%±5% RH until mortality evaluations were made, 48 hours after treatment.

| Compound Numbers | % Control (48 hrs) |
|---|---|
| 1 | 90 |
| 2 | 100 |
| 3 | 100 |
| 4 | 100 |
| 5 | 100 |
| 7 | 95 |

EXAMPLE 27

Red kidney bean leaf discs were infested with adult female two-spotted spider mites. Leaves with 20-30 mites were chosen for testing. Test leaves were removed from the plant and inverted, thereby exposing the mites to direct spray, and held in place by an insect pin protruding up from the test rack. The mites were sprayed with a 75:25 acetone:water solution of the compounds listed below at a rate of 0.5 lb. a.i./acre using a hydraulic nozzle. Treated leaf discs were placed upper surface down on a piece of water-soaked cotton housed in a plastic petri dish. Test units were held at 27°±1° C. and 48%±5% RH, and mortality evaluations were made 48 hours after treatment.

| Compound Numbers | % Control (48 hrs) |
|---|---|
| 6 | 100 |
| 8 | 100 |
| 9 | 100 |
| 10 | 100 |
| 11 | 100 |

EXAMPLE 28

Activity against the southern corn rootworm was demonstrated using test unit consisting of an 8-oz. plastic cup containing 2 sprouted corn seeds. The test unit was sprayed with a 75:25 acetone:distilled water solution of the compounds listed below using a flat fan hydraulic nozzle at a rate of 0.5 lb. a.i./acre. After treatment, the sprayed cups were allowed to dry, ten (10) second or third instar rootworm larvae were placed in each test cup, and the cups were capped. Test units were held at 27°±1° C. and 48%±5% RH. Mortality evaluations made 48 hours after treatment.

| Compound Numbers | % Control (48 hrs) |
|---|---|
| 6 | 100 |
| 8 | 100 |
| 9 | 100 |
| 10 | 100 |
| 11 | 100 |

It will be apparent that the instant specification and examples are set forth by way of illustration and not limitation, and that various modifications and changes may be made without departing from the spirit and scope of the present invention.

What is claimed is:

1. A compound having the formula:

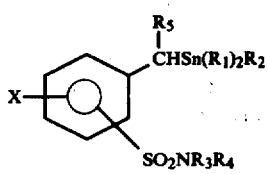

wherein
R₁ and R₂ are independently $C_1$-$C_3$ alkyl;
R₃ is H, $OCH_3$, $C_1$-$C_{20}$ alkyl, $C_5$-$C_6$ cycloalkyl optionally substituted with $CH_3$ or $OCH_3$, $C_1$-$C_3$ alkyl substituted with $OCH_3$ or $OC_2H_5$, or

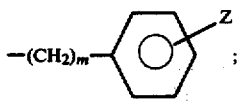

R₄ is H, $C_1$-$C_{20}$ alkyl, $C_5$-$C_6$ cycloalkyl optionally substituted with $CH_3$ or $OCH_3$, $C_1$-$C_3$ alkyl substituted with $OCH_3$ or $OC_2H_5$; or

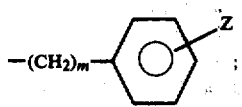

or R₃ and R₄ may be taken together to form

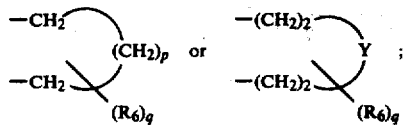

R₅ is H or $CH_3$;
R₆ is $CH_3$;
X is H, F, Cl, $CH_3$ or $OCH_3$;
Y is O or $NR_7$;
Z is H, F, Cl, $CH_3$ or $OCH_3$;
R₇ is $C_1$-$C_3$ alkyl;
m is 0 or 1;
p is 2, 3 or 4; and
q is 0, 1 or 2;
or an agriculturally suitable salt thereof; provided that:
(1) the total number of carbons in R₃ and R₄ is less than or equal to 20;
(2) when either R₃ or R₄ is

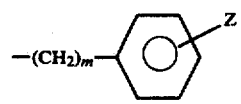

and the other is alkyl, the total number of carbons in R₃ and R₄ is less than or equal to 12; and
(3) when R₃=$OCH_3$, then R₄=H or $C_1$-$C_4$ alkyl.

2. A compound of claim 1 wherein R₁=R₂ and R₅ is H.
3. A compound of claim 2 wherein X is H.
4. A compound of claim 3 wherein
R₁ and R₂ are $CH_3$;
R₃ is H, $OCH_3$, $C_1$-$C_{20}$ alkyl, $C_5$-$C_6$ cycloalkyl optionally substituted with $CH_3$ or $OCH_3$, $CH_2CH_2OCH_3$, $CH_2CH_2OC_2H_5$, $CH_2CH_2CH_2OCH_3$, $CH_2CH_2CH_2OC_2H_5$, or

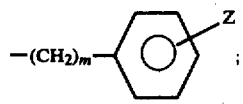

and
R₄ is H, $C_1$-$C_{20}$ alkyl, $C_5$-$C_6$ cycloalkyl optionally substituted with $CH_3$ or $OCH_3$, $CH_2CH_2OCH_3$, $CH_2CH_2OC_2H_5$, $CH_2CH_2CH_2OCH_3$, or $CH_2CH_2CH_2OC_2H_5$;
or R₃ and R₄ may be taken together to form

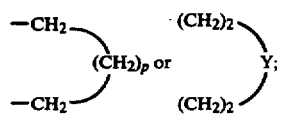

Y is O or $NCH_3$; and
p is 2 or 3.

5. A compound of claim 1 which is 2-[(trimethylstannyl)methyl]benzenesulfonamide.
6. A compound of claim 1 which is N-methyl-2-[(trimethylstannyl)methyl]benzenesulfonamide.
7. A compound of claim 1 which is N,N-dimethyl-2-[(trimethylstannyl)methyl]benzenesulfonamide.
8. A compound of claim 1 which is N-butyl-2-[(trimethylstannyl)methyl]benzenesulfonamide.
9. A compound of claim 1 which is N-(1,1-dimethylethyl)-2-[(trimethylstannyl)methyl]benzenesulfonamide.
10. A compound of claim 1 which is N-ethyl-N-methyl-2-[(trimethylstannyl)methyl]benzenesulfonamide.
11. A compound of claim 1 which is N,N-dihexyl-2-[(trimethylstannyl)methyl]benzenesulfonamide.
12. A compound of claim 1 which is N-phenyl-2-[(trimethylstannyl)methyl]benzenesulfonamide.
13. A compound of claim 1 which is 4-[2-[(trimethylstannyl)methyl]phenylsulfonyl]morpholine.
14. A compound of claim 1 which is 1-[2-[(trimethylstannyl)methyl]phenylsulfonyl]pyrrolidine.
15. A compound of claim 1 which is N-dodecyl-2-[(trimethylstannyl)methyl]benzenesulfonamide.
16. A compound of claim 1 which is N-methyl-4-[(trimethylstannyl)methyl]benzenesulfonamide.
17. A compound of claim 1 which is N,N-dimethyl-4-[(trimethylstannyl)methyl]benzenesulfonamide.
18. A compound having the formula:

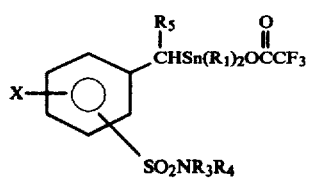

wherein
R₁ is $C_1$-$C_3$ alkyl;
R₃ is H, $OCH_3$, $C_1$-$C_{20}$ alkyl, $C_5$-$C_6$ cycloalkyl optionally substituted with $CH_3$ or $OCH_3$, $C_1$-$C_3$ alkyl substituted with $OCH_3$ or $OC_2H_5$, or

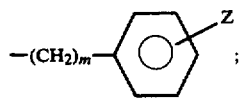

R$_4$ is H, C$_1$–C$_{20}$ alkyl, C$_5$–C$_6$ cycloalkyl optionally substituted with CH$_3$ or OCH$_3$, C$_1$–C$_3$ alkyl substituted with OCH$_3$ or OC$_2$H$_5$, or

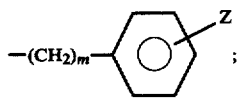

or R$_3$ and R$_4$ may be taken together to form

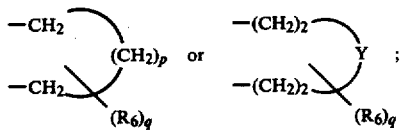

R$_5$ is H or CH$_3$;
R$_6$ is CH$_3$;
X is H, F, Cl, CH$_3$ or OCH$_3$;
Y is O or NR$_7$;
Z is H, F, Cl, CH$_3$ or OCH$_3$;
R$_7$ is C$_1$–C$_3$ alkyl;
m is 0 or 1;
p is 2, 3 or 4; and
q is 0, 1 or 2;
provided that:
(1) the total number of carbons in R$_3$ and R$_4$ is less than or equal to 20;
(2) when either R$_3$ or R$_4$ is

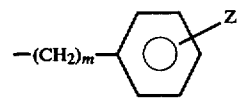

and the other is alkyl, the total number of carbons in R$_3$ and R$_4$ is less than or equal to 12;
(3) when R$_3$=OCH$_3$, then R$_4$=H or C$_1$–C$_4$ alkyl.

19. A composition suitable for the control of insects and arachnids which comprises an insecticidally or arachnicidally effective amount of a compound of any one of claims 1 through 17 and a diluent, surfactant, or mixtures thereof.

20. A method for the control of insects and arachnids which comprises applying to the insects or arachnids, to a habitat thereof, or to a locus to be protected an insectidially or arachnicidally effective amount of a compound of any one of claims 1 through 17.

* * * * *